US009498161B1

(12) United States Patent
Sunden et al.

(10) Patent No.: US 9,498,161 B1
(45) Date of Patent: Nov. 22, 2016

(54) SMALL FORM-FACTOR PRESSURE SENSOR PASSAGES

(71) Applicant: Fitbit, Inc., San Francisco, CA (US)

(72) Inventors: Lindsey Michelle Sunden, San Francisco, CA (US); Jung Ook Hong, San Jose, CA (US); Shelten Gee Jao Yuen, Berkeley, CA (US); Michael Joseph Francisco, Fremont, CA (US); Samuel Paul Martino, San Francisco, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 14/885,817

(22) Filed: Oct. 16, 2015

(51) Int. Cl.
*G01C 5/06* (2006.01)
*A61B 5/00* (2006.01)

(52) U.S. Cl.
CPC ............... *A61B 5/681* (2013.01); *G01C 5/06* (2013.01); *A61B 2560/0257* (2013.01); *A61B 2562/0247* (2013.01)

(58) Field of Classification Search
None
See application file for complete search history.

(56) References Cited

U.S. PATENT DOCUMENTS

| | | | | |
|---|---|---|---|---|
| 2014/0135612 A1* | 5/2014 | Yuen | ................ | A61B 5/02405 600/407 |
| 2014/0174958 A1* | 6/2014 | Martinez | ................ | G06F 15/00 206/37 |
| 2014/0180019 A1* | 6/2014 | Martinez | ............ | A61B 5/02055 600/301 |
| 2014/0196539 A1* | 7/2014 | Martinez | ................ | G06F 15/00 73/384 |
| 2014/0288435 A1* | 9/2014 | Richards | ............ | A61B 5/02427 600/479 |
| 2015/0122018 A1* | 5/2015 | Yuen | ................ | G01B 21/16 73/384 |
| 2015/0366518 A1* | 12/2015 | Sampson | ............... | A61B 5/747 600/301 |
| 2016/0051167 A1* | 2/2016 | Saha | ................ | A61B 5/1123 702/141 |
| 2016/0051169 A1* | 2/2016 | Hong | ................ | A61B 5/1123 600/595 |

OTHER PUBLICATIONS

"Summary of Fitbit Products with Channels for Pressure Sensors Sold Prior to Oct. 16, 2015," 13 pages including a summary of each product and drawings, Fitbit, Inc., San Francisco, California.
News Release by Applicant dated Oct. 10, 2013 for the Fitbit Force entitled "Fitbit Debuts Force—the Most Advanced Wireless Activity and Sleep-Tracking Wristband Yet", which is located at: https://investor.fitbit.com/press/press-releases/press-release-details/2013/Fitbit-Debuts-Force--the-Most-Advanced-Wireless-Activity-and-Sleep-Tracking-Wristband-Yet/default.aspx.
News Release by Applicant dated Oct. 27, 2014 for the Fitbit Charge, Charge HR, and Surge entitled "Fitbit Announces Fitbit Charge, Fitbit Charge HR and Fitbit Surge—3 New Fitness Trackers for Everyday, Active and Performance Consumers" which is located at https://investor.fitbit.com/press/press-releases/press-release-details/2014/Fitbit-Announces-Fitbit-Charge-Fitbit-Charge-Hr-and-Fitbit-Surge---3- New-Fitness-Trackers-for-Everyday-Active-and-Performance-Consumers/default.aspx.

* cited by examiner

Primary Examiner — Andre Allen
(74) Attorney, Agent, or Firm — Weaver Austin Villeneuve & Samson LLP

(57) ABSTRACT

Passages for communicating ambient air to a pressure sensor within a housing are provided; such passages may have particular cross-sectional characteristics that result in higher-quality pressure data having less noise than may be obtained used passages having other cross-sectional characteristics.

30 Claims, 17 Drawing Sheets

SMALL FORM-FACTOR PRESSURE SENSOR PASSAGES

BACKGROUND

Personal fitness and health monitoring devices, which may be referred to as biometric monitoring devices herein, may include a variety of different sensors that are used to provide feedback regarding various physiological characteristics of a person. Such sensors may include, but are not limited to, pressure sensors used to track elevation gain.

SUMMARY

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale unless specifically indicated as being scaled drawings.

In some implementations, a wearable biometric monitoring device may be provided that includes a pressure sensor, a housing that includes a first vent, and a first passage in the housing. In such implementations, the first passage may provide a first path from the first vent to the pressure sensor and may have a first cross-section in a plane perpendicular to the first path at at least a first point along the first path. The first cross-section may have a first dimension in a first direction and a second dimension in a second direction orthogonal to the first direction, and the first dimension may be at least one and a half times as large as the second dimension.

In some implementations, the first dimension may be 2 mm or more.

In some implementations, the first direction may be tangent to the average exterior surface of the housing at a location closest to the first point.

In some implementations, the first dimension may be between 2 mm and 4 mm and the second dimension may be between 0.3 mm and 1 mm.

In some implementations, the first path may have a path length of at least 2 mm.

In some implementations, the first dimension may be greater than 1 mm.

In some implementations, the first passage may allow air external to the wearable biometric monitoring device to travel from the first vent to the pressure sensor.

In some implementations, a portion of an exterior surface of the housing may form a recess, and the first vent may be located in the recess.

In some such implementations, the recess may be located in the exterior surface of the housing such that the exterior surface of the housing immediately surrounding the recess is adjacent to, and faces towards, a person's skin when the wearable biometric monitoring device is worn. The housing may further includes a second passage and a second vent that is located on the exterior surface of the housing in a location that is not adjacent to, and does not face towards, the person's skin when the wearable biometric monitoring device is worn. The second passage may provide a second path from the recess to the second vent and may allow air pressure external to the wearable biometric monitoring device to travel from the second vent to the recess. The second passage may have a second cross-section in a plane perpendicular to the second path at at least a second point along the second path, and the second cross-section may have a third dimension in a third direction and a fourth dimension in a fourth direction orthogonal to the third direction; the third dimension may be at least one and a half times as large as the fourth dimension.

In some further such implementations, the recess may be configured to allow pressure to travel between the first passage to the second passage even when the wearable biometric monitoring device is worn by the person and the exterior surface of the housing immediately surrounding the recess is thereby covered by the person's skin.

In some additional or alternative such implementations, the recess may include a protrusion within the recess, a gap may exist between the protrusion and the sidewalls of the recess, the gap may have a gap depth defined by either a height of the protrusion or a depth of the recess and a gap width defined by an offset distance between the sidewalls and the protrusion, and the gap depth may be at least one and a half times as large as the gap width.

In some implementations, the second path may be straight. In some other implementations, the second path may follow a 2-dimensional curve in a plane normal to the first direction.

In some implementations, the housing may include a housing body and a cover piece, the second vent may be located on the cover piece, and the first passage and the second passage may, at least in part, be defined by surfaces of the housing body and the cover piece when the cover piece is assembled to the housing body.

In some such implementations, the first path may follow an interior surface of the cover piece.

In some implementations, the first dimension may be at least one and a half times the second dimension for the first cross-section at first points located along at least 90% of the first path.

In some implementations, the first cross-section may vary in shape, size, or dimension along at least a portion of the first path.

In some implementations, the first path may be straight; in other implementations, the first path may follow a 2-dimensional curve in a plane normal to the first direction.

In some implementations, the first cross-section may be substantially rectangular or rectangular with internal fillets.

In some implementations, the housing may include a second vent, the first vent may be located at a first location on an outer surface of the housing, the second vent may be located at a second location on the outer surface of the housing, and the first passage may provide a first path from the second vent to the pressure sensor. In such implementations, the first passage may allow air external to the wearable biometric monitoring device to travel from the first vent to the pressure sensor, and the first passage may also allow air external to the wearable biometric monitoring device to travel from the second vent to the pressure sensor.

In some such implementations, the first dimension may be at least three times as large as the second dimension.

In some implementations, the housing may include a housing body and a cover piece, and the first passage may, at least in part, be defined by surfaces of the housing body and the cover piece when the cover piece is assembled to the housing body. In such implementations, the first vent may extend through the cover piece, the second vent may extend through the cover piece or the housing body, and the first location may be located such that the first vent is not facing into a person's skin when the wearable biometric monitoring device is worn.

In some implementations, a wearable biometric monitoring device may be provided that includes a pressure sensor and a housing. The housing may include a pressure sensor plenum volume in fluidic communication with the pressure sensor, a first passage, with a first vent on an exterior surface of the housing, that allows air pressure external to the wearable biometric monitoring device to travel from the first vent to the pressure sensor, a second passage, with a second vent on the exterior surface of the housing, that allows air pressure external to the wearable biometric monitoring device to travel from the second vent to the pressure sensor, a third passage, with a third vent on the exterior surface of the housing, that allows air pressure external to the wearable biometric monitoring device to travel from the third vent to the pressure sensor, and a fourth passage, with a fourth vent on the exterior surface of the housing, that allows air pressure external to the wearable biometric monitoring device to travel from the fourth vent to the pressure sensor. The first passage may extend away from the pressure sensor plenum volume in a first direction, the second passage may extend away from the pressure sensor plenum volume in a second direction, the third passage may extend away from the pressure sensor plenum volume in a third direction, and the fourth passage may extend away from the pressure sensor plenum volume in a fourth direction. Moreover, the first passage may have a first dimension in a third direction and a corresponding second dimension in a fourth direction orthogonal to the third direction, the second passage may have a third dimension in a fifth direction and a corresponding fourth dimension in a sixth direction orthogonal to the fifth direction, the third passage may have a fifth dimension in a seventh direction and a corresponding sixth dimension in a eighth direction orthogonal to the seventh direction, and the fourth passage may have a seventh dimension in a ninth direction and a corresponding eighth dimension in a tenth direction orthogonal to the ninth direction. Two or more of the first dimension, the third dimension, the fifth dimension, and the seventh dimension may be within ±10% of each other, and two or more of the second dimension, the fourth dimension, the sixth dimension, and the eighth dimension may be within ±10% of each other.

In some such implementations, the first passage, the second passage, the third passage, and the fourth passage may all have substantially circular cross-sections with cross-sectional areas of less than 1 square millimeter.

In some implementations, the first direction and the second direction may be parallel paths within the housing, and the third direction and the fourth direction may also be parallel paths within the housing.

In some implementations, one or more of the first passage, the second passage, the third passage, and the fourth passage may have a semicircular cross-section.

In some implementations, more than one of the first direction, the second direction, the third direction, and the fourth direction may be parallel with one another.

In some implementations, three or more of the first dimension, the third dimension, the fifth dimension, and the seventh dimension may be within ±10% of each other, and three or more of the second dimension, the fourth dimension, the sixth dimension, and the eighth dimension may be within ±10% of each other.

BRIEF DESCRIPTION OF THE DRAWINGS

The various implementations disclosed herein are illustrated by way of example, and not by way of limitation, in the figures of the accompanying drawings, in which like reference numerals refer to similar elements.

DETAILED DESCRIPTION

Figure 1:
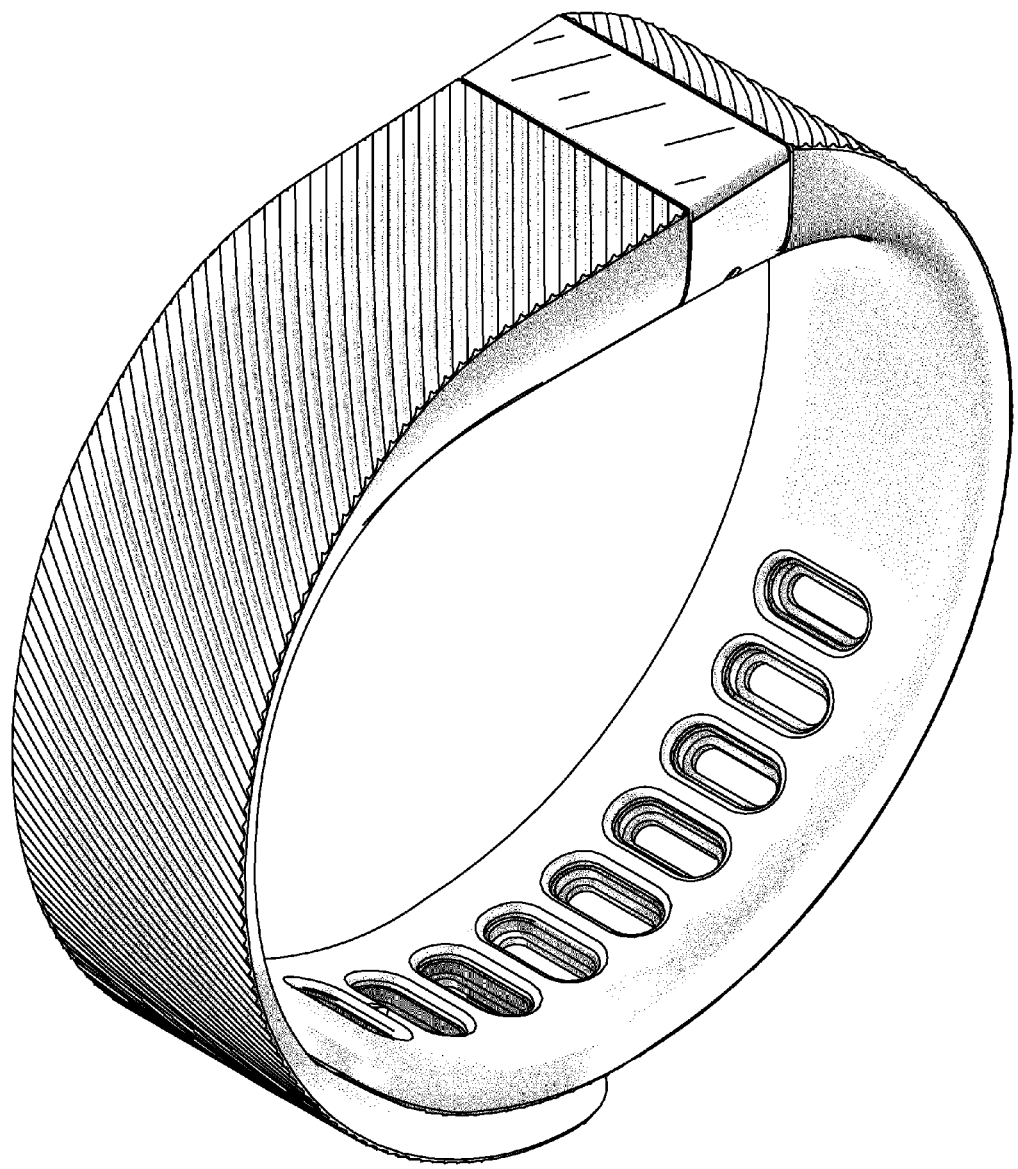
FIG. 1 depicts an isometric view of a first example wrist-wearable biometric monitoring device.

The present disclosure relates to pressure sensor passage design for biometric monitoring devices (also referred to herein as "biometric tracking devices," "biometric tracking modules," "wearable fitness monitors," or the like). More specifically, the present disclosure is directed to pressure sensor passage design usable in small form factor housings of biometric monitoring devices. As used herein, "biometric monitoring device" may include biometric monitoring devices that are worn by a user, e.g., a wearable biometric monitoring device. Some biometric monitoring devices may track elevation gain through the use of a pressure sensor, e.g., a barometer or altimeter, mounted in the biometric monitoring device. Generally speaking, in order to measure altitude gains/losses, pressure sensors require exposure to ambient air in order to measure the ambient air pressure external to the biometric monitoring device and thus determine altitude changes.

The present inventors determined that for internally-mounted pressure sensors in wearable biometric monitoring devices, it may be advantageous to provide a fluidic connection between the ambient environment and the pressure sensor through the use of one or more passages within the housing of the biometric monitoring device. As used herein, a "fluidic connection" may mean a connection between two or more spaces, e.g. volumes, which may allow a fluid, e.g. a gas or liquid, to travel or flow between the two or more spaces or volumes. Such a passage may, for example, provide a fluidic connection between a vent or port on an external surface of the housing and a plenum or volume internal to the biometric monitoring device adjacent to where the pressure sensor is mounted. The present inventors have determined that, in some cases, it may be beneficial for the vent or other opening that connects with such a passage to be located in a position that is offset from a person's skin when the biometric monitoring device is worn to reduce the instances in which the person's skin occludes the vent or opening.

The present inventors also determined that particular geometric aspects of such passages may be controlled in order to prevent certain undesirable side effects. The present inventors have determined improvements to the passages of a wearable biometric monitoring device that connect the pressure sensor with the air that is external to the wearable biometric monitoring device (also referred to herein as a "pressure sensor passage"). Some pressure sensor passages may be located in the housing of a wearable biometric monitoring device and may connect to the ambient environment at a vent.

Many consumer electronics, including wearable biometric monitoring devices, are small form factor devices which manufacturers are attempting to make smaller and lighter while still keeping such designs aesthetically pleasing, marketable, economically manufacturable, and functional. For example, in a typical wrist-wearable biometric monitoring device, the device housing may measure approximately 0.375" thick or less, 1" wide or less, and 1.5" long or less. The concepts discussed herein are not limited to device housings of such a size, however. Such a housing may provide a rigid, protective cover around the internal components housed inside, which may include, depending on the capabilities of the biometric monitoring device, a battery or other energy storage unit, a display, a vibramotor, one or more processors, memory, a charging or data connector port, an inductive charger system, a Bluetooth or other wireless antenna, an accelerometer, a gyroscope, a heart rate sensor, and/or a pressure sensor. As a result of this, wearable biometric monitoring devices may have limited space and configurability for their elements, including the pressure sensor and pressure sensor passage(s). The concepts and ideas discussed herein may also be applied in other contexts, including smartphones, GPS units, and other devices that may utilize pressure sensors.

The present inventors determined that, for packaging and aesthetic considerations, it would be beneficial to locate the pressure sensor for a biometric monitoring device within the housing such that the pressure-sensing element of the pressure sensor was oriented towards the wearer's skin (for example, many commercially-available surface-mount pressure sensors have pressure-sensing elements that are parallel to the mounting plane of the surface-mount pressure sensor—since the printed circuit boards that such sensors may be mounted to may often be generally parallel to the wearer's skin as well, this may, in part, govern the mounting orientation of the pressure sensor). While such a pressure sensor could be mounted in the opposite direction, i.e., facing away from the person's skin, the most logical location for a vent for such a pressure sensor would be on the upper surface of the biometric monitoring device, which is typically the most visible portion of the biometric monitoring device when the biometric monitoring device is worn by a person. It may not be aesthetically pleasing to have such a vent so prominently visible. While the concepts disclosed herein are discussed within the context of a biometric monitoring device with a pressure sensor mounted in a similar orientation to that discussed above, it is to be understood that the concepts discussed herein are equally applicable to pressure sensors mounted in other orientations or locations within a biometric monitoring device.

In some biometric monitoring device design, a pressure sensor may be included within the device housing and oriented such that the pressure sensor's pressure-sensitive area faced towards the wearer's wrist when the biometric monitoring device is worn; two small holes or vents may pass through the device housing at the location of the pressure sensor to allow the pressure sensor to connect with the ambient air around the biometric monitoring device. There may be no passages within the device housing that provide fluidic connections between the vents and the pressure sensor in such a design. Since the vents in such a design exit the device housing at a location that would be placed against the wearer's skin when the biometric monitoring device is worn, two small, parallel channels or grooves, each terminating at one of the vents, may be included in the exterior surface of the device housing. These grooves, which may be, for example, approximately 0.9 mm deep by 0.9 mm wide, may travel from the vent locations, which may be both located along the centerline of the housing on the wrist-facing surface of the housing, in a direction generally parallel to the person's forearm, and end near the side of the biometric monitoring device adjacent to the skin-facing surface of the biometric monitoring device.

The present inventors determined that this configuration where the channels or grooves are located on the external surface resulted in some unexpected and undesirable side effects. First, when the wearer's skin became moist, the skin would seal against the vents—despite the presence of the grooves—and this seal would prevent equalization between the ambient environment air and the air within the device housing at the location of the pressure sensor. Moreover, as the wearer moved about, the biometric monitoring device might repeatedly shift on the person's wrist, causing this seal to be repeatedly broken and re-formed. The fluctuations in pressure caused by such sealing/re-sealing caused the pressure data recorded by the pressure sensor to exhibit a large degree of noise, which complicated the calculation of altitude, and thus changes in altitude. In addition to the issues caused by the interaction of the wearer's skin with the vents, the present inventors also determined that the vents themselves presented a problem in that, due to their small size, it was easy for a droplet of moisture, e.g., sweat, to become trapped in the vent due to capillary forces. The inventors determined that when such a droplet became trapped, it effectively turned into a membrane that separated the pressure sensor from the ambient environment. When exposed to motion, e.g., such as when the wearer moved their arm, this droplet membrane would move within the vent due to inertial effects, causing the volume trapped between the membrane and the pressure sensor to fluctuate, which, in turn, caused pressure fluctuations that introduced further noise into the pressure sensor data. In some cases, such noise would be of sufficient magnitude that "false floors" would register, e.g., if the biometric monitoring device included the ability to determine the number of flights of stairs climbed based, at least in part, on the pressure sensor data, the biometric monitoring device might falsely indicate that a flight of stairs had been climbed due to the pressure signal noise.

After discovering these issues, the present inventors conceived of a solution in which the pressure sensor was placed within the housing of the device, a pressure sensor passage (also referred to herein simply as a "passage") was provided within the housing, and a vent was located on an exterior surface of the housing in order to allow air external to the wearable biometric monitoring device to travel from the external environment, through the vent and into the passage, through the passage, and then to the pressure sensor. The inclusion of the passage allowed the vent to be re-located to a position that did not result in direct and regular contact with the wearer's skin even though the location of the pressure sensor could be left relatively unchanged.

In addition to conceiving of the addition of such a passage, the present inventors determined that passages having particular cross-sectional characteristics provided unexpectedly superior performance as compared with passages not possessing such characteristics. For example, the present inventors determined that passages with non-square cross-sections, at least at scales suitable for implementation in a wearable biometric monitoring device, e.g., having sub-millimeter or millimeter-level dimensions, may offer superior performance as compared with passages having "square" cross-sections, e.g., square passages, circular passages, etc. The present inventors determined that passages having cross-sectional dimensional ratios of 2:1 or greater, at least in housings made with polycarbonate or ABS plastic, may exhibit particularly superior resistance to interference on the part of moisture droplets that may be trapped within the passage. In some cases, the ratios may be as low as 1.5:1, 1.6:1, 1.7:1, 1.8:1, or 1.9:1 or greater. While most of the examples discussed herein focus on implementations in which this ratio is 2:1 or greater, it is to be understood that it is expressly contemplated herein that these examples may be modified so as to have a 1.5:1 ratio or higher. In some implementations, the cross-sectional dimensional ratios may be approximately 2:1 or greater, i.e., 2:1±10% or greater.

Figure 2:
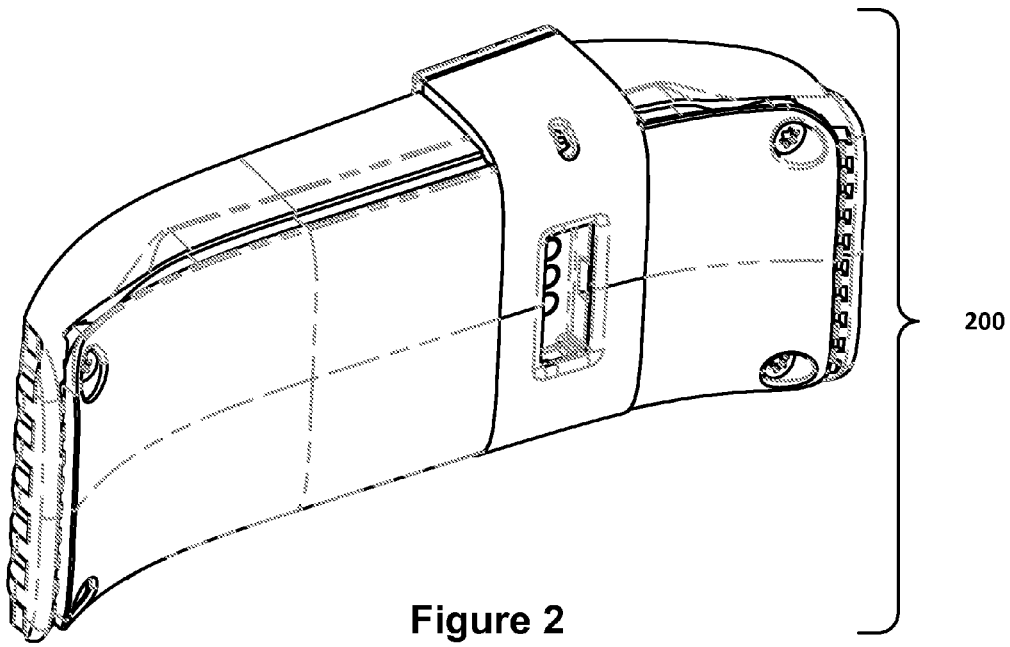
FIG. 2 depicts an isometric view of the housing for the first example wrist-wearable wearable biometric monitoring device of FIG. 1.
Figure 3:
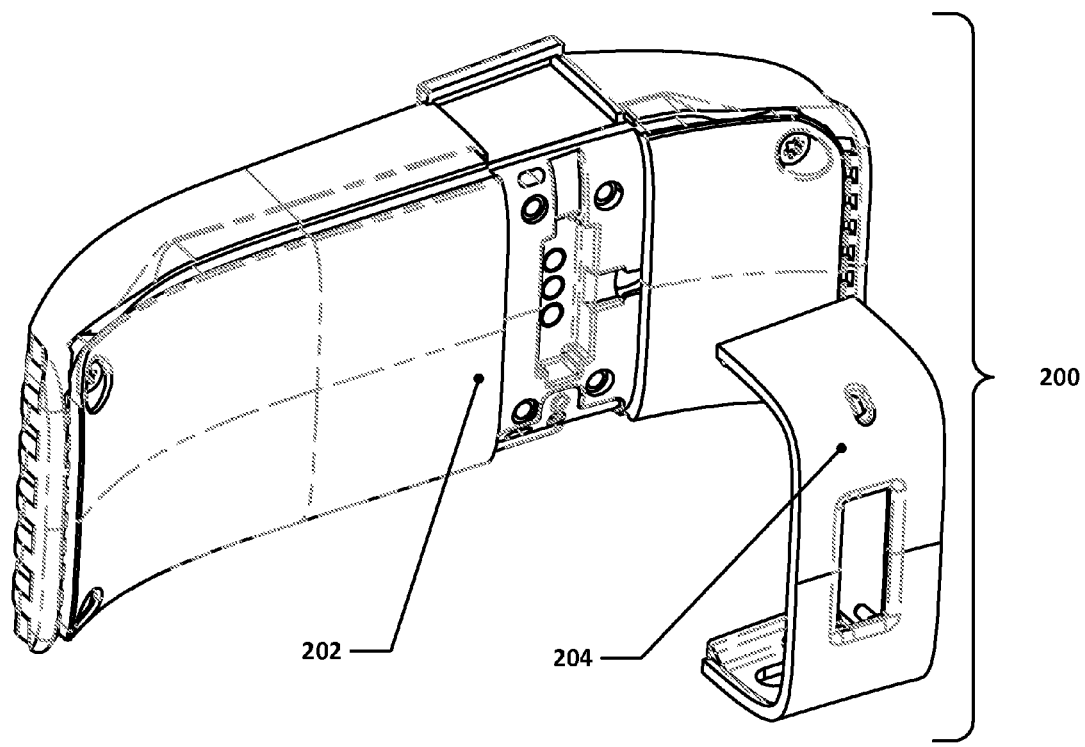
FIG. 3 depicts an isometric, partially exploded view of the housing for the first example wearable biometric monitoring device of FIG. 2.

FIG. 1 depicts an isometric view of a first example wrist-wearable biometric monitoring device. FIG. 2 depicts an isometric view of the housing for the first example wrist-wearable wearable biometric monitoring device of FIG. 1. FIG. 3 depicts an isometric, partially exploded view of the housing for the first example wearable biometric monitoring device of FIG. 2. As can be seen, the housing 200 includes a housing body 202 and a cover piece 204. In some implementations, the cover piece 204 may be assembled to the housing body 202 by a number of methods known in the art including, but not limited to, adhesion, bonding, screws, clips, heat-melted pins, etc., or a combination of any such methods. The cover piece 204 may be located adjacent to the housing body 202 such that one or more portions of the cover piece 204 overlap with and/or cover one or more portions of the housing body 202. The cover piece may provide both decorative and functional features. It is to be understood that in some other implementations, the housing may be a single-piece housing, e.g., formed as a single injection-molded part, rather than a housing assembled out of two or more discrete parts.

The first example wearable biometric monitoring device may include a pressure sensor that may be embedded within the housing 200. As discussed above, some pressure sensors require a fluidic connection with ambient air of an environment surrounding the wearable biometric monitoring device in order to function as altimeters. In some implementations of the present invention, the housing 200 may include a first passage that allows ambient air that is external to the wearable biometric monitoring device to travel to the pressure sensor that may be housed within the housing 200. In some implementations, the housing 200 may also include a second passage that allows ambient air that is external to the wearable biometric monitoring device to travel to the pressure sensor; the second passage may be an alternate air route from the first passage, or may form an extension, in effect, of the first passage. As discussed below, the first passage and/or second passage may be formed within only the housing body 202 or may be formed by both the housing body 202 and the cover piece 204, e.g., where a portion of a passage is formed by the housing body 202 and a remaining portion of the passage is formed by the cover piece 204. In other implementations, it is conceivable that the passages discussed herein may be formed in other pieces as well, depending on the specific configuration of the biometric monitoring device in question (for example, such passages may be formed in a flexible strap that is connected with the housing).

Figure 4:
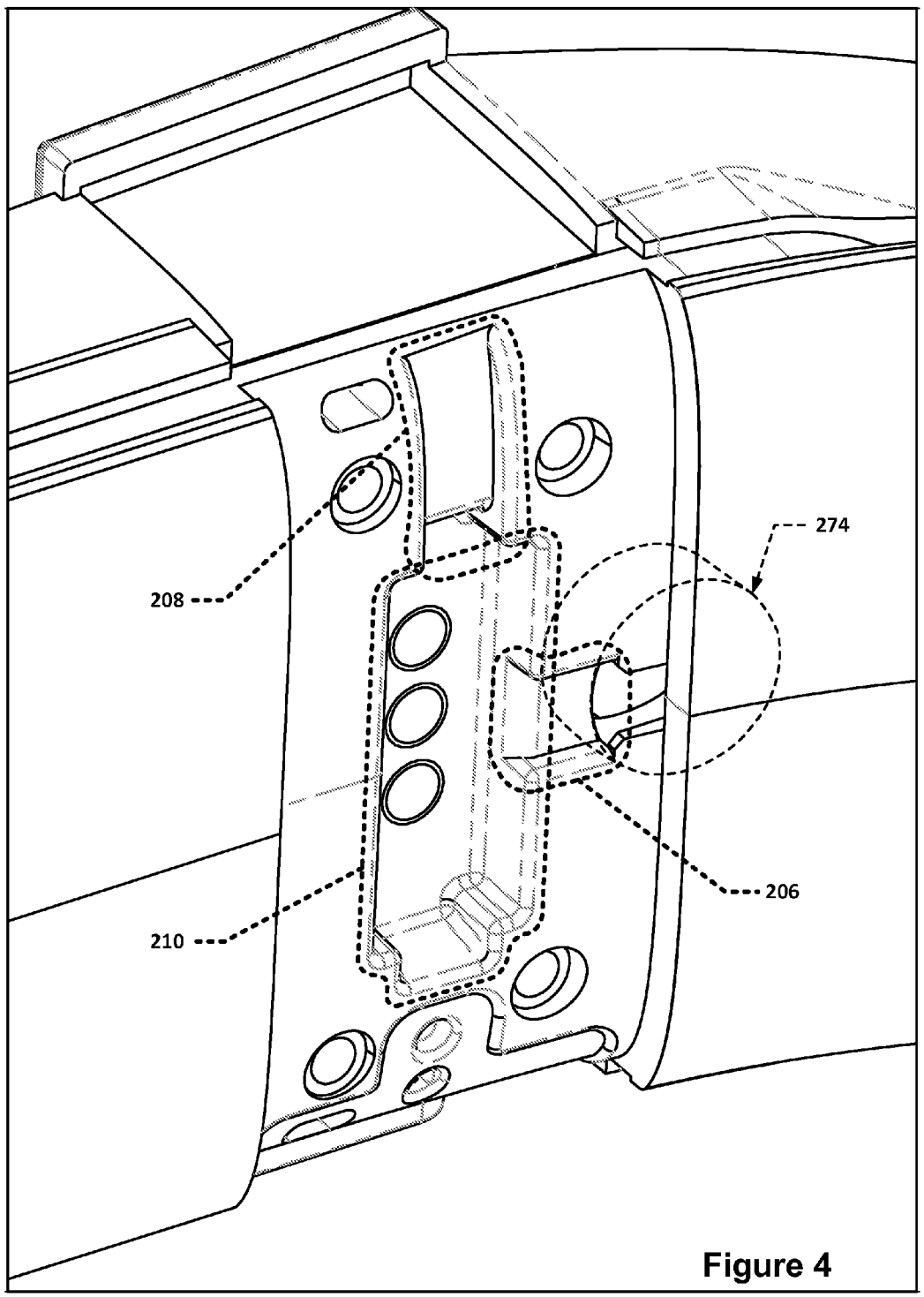
FIG. 4 depicts a close-up isometric view of a portion of the exploded housing body of FIG. 3.
Figure 5:
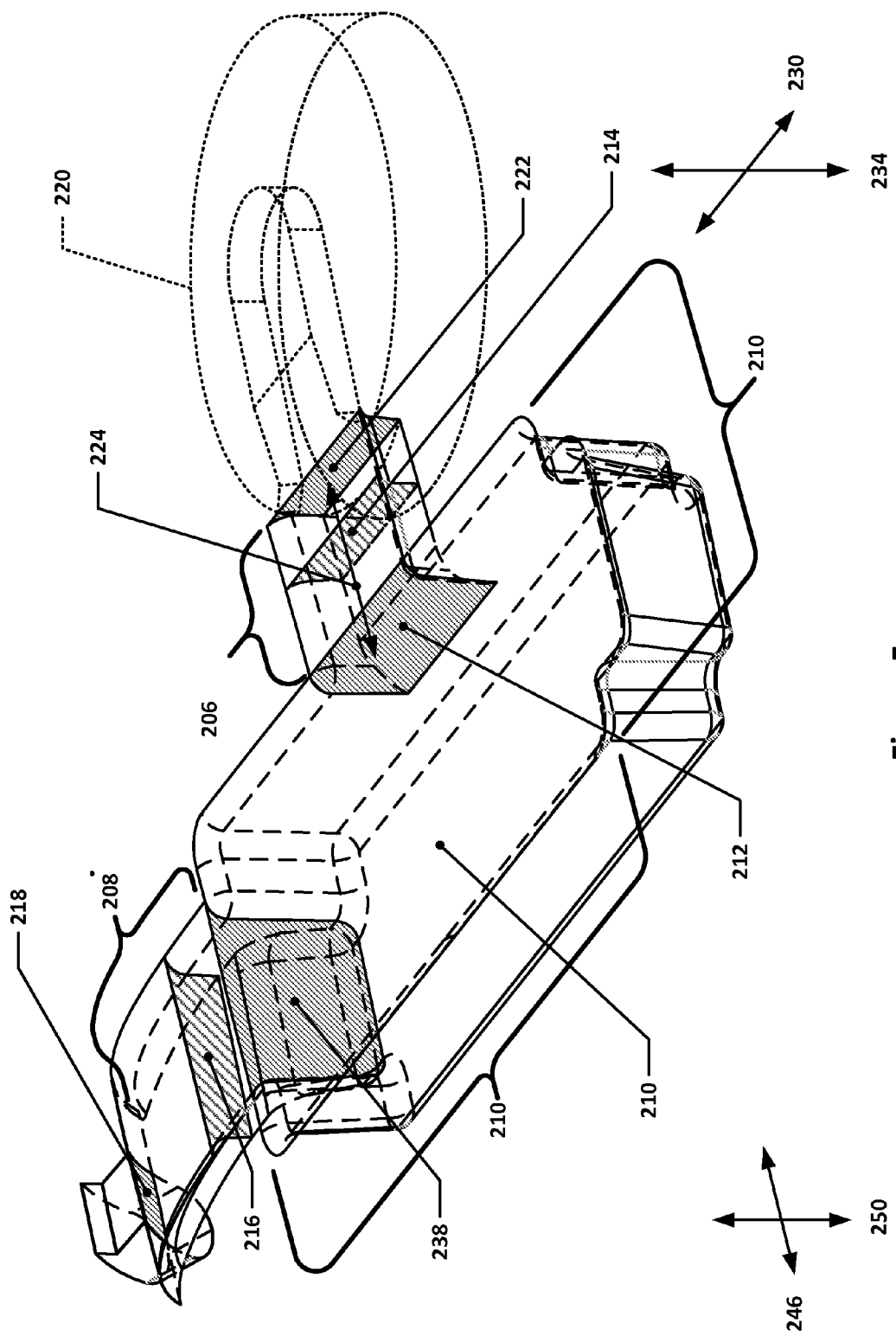
FIG. 5 is a representation of the "empty space" within the housing through which air may flow in order to reach the pressure sensor.

In the implementation shown in FIG. 3, the first passage and the second passage may be formed by surfaces from both the housing body 202 and the cover piece 204. FIG. 4 depicts a close-up isometric view of a portion of the exploded housing body 202 of FIG. 3. As can be seen, the cover piece 204 has been removed from the housing body 202 to expose a part of the housing body 202 and show that the housing body 202 includes a first passage 206, a second passage 208, and a recess 210. The location of a pressure sensor 274 is indicated by dashed lines within the housing body 202. Discussed further below, FIG. 5 depicts the volumetric representation of the first passage 206, second passage 208, and recess 210 of housing 200. In other words, FIG. 5 is a representation of the "empty space" within the housing 200 through which air may flow in order to reach the pressure sensor.

In some implementations, more than one surface of the first passage 206 may be formed by the housing body 202 such that the first passage 206 may be an open channel in the housing body 202. As depicted in FIG. 4, the first passage 206 is an open channel with three sides formed by the housing body 202. The first passage 206 may be connected to the recess 210, as also shown in FIG. 4. The recess 210 may, for example, be a data or power plug receptacle. Similarly, the second passage 208 may be formed within the housing 200 such that more than one surface of the second passage 208 may be formed in the housing body 202, e.g., like a channel with three sides formed by the housing body 202 as in FIG. 4, and the second passage 208 may also be connected to the recess 210.

In some such implementations, when the cover piece 204 is secured to the housing body 202, one or more surfaces of the first passage 206 may be provided by the cover piece 204. Therefore, in FIG. 4, the fourth side of the first passage 206 may be formed by the cover piece 204 which may act as a "top" to the first passage 206. The fourth side of the second passage 208 may also be formed by the cover piece 204, e.g., creating a "top" to the second passage 208.

As stated above, in some implementations the first passage 206 and/or the second passage 208 may be fully formed within the housing body 202. In some such implementations, all sides of the first passage 206 and/or the second passage 208 may be formed by the housing body 202 such that no sides are formed or bounded by the cover piece 204. In some other implementations, one or more surfaces of the first passage 206 and/or the second passage 208 may be formed within the housing body 202 and one or more surfaces of the first passage 206 and/or the second passage 208 may be formed by and/or within the cover piece 204. For instance, three sides of a first passage 206 may be formed within the cover piece 204, e.g., the first passage 206 is a channel in the cover piece 204, while the fourth and final side of the first passage 206 may be formed by the housing body 202.

Additionally, in some implementations, the first passage and/or the second passage may have more or less than four sides. For example, the first passage may be substantially elliptical such that it may only have "one" clearly recognizable "side," or the first passage may have five or six discernable sides. In some such implementations, the surface or surfaces of the first passage may be fully formed by the housing body and not by the cover piece. In some other such implementations, the surface or surfaces of the first passage may be partially formed by the housing body and partially formed by the cover piece, thereby creating a fully formed first passage within the housing.

The first passage and/or second passage may have any number of cross-sectional boundaries and shapes like those implementations discussed below and illustrated in at least FIGS. 9 through 16. For instance, the passages may be elliptical, rectangular, and rectangular with curved corners.

Some configurations of housing 200, including that of the housing body 202, first passage 206, second passage 208, and recess 210, partially shown in FIGS. 2 to 4, will now be discussed. As discussed, FIG. 5 depicts a volumetric representation of the first passage 206, the second passage 208, and the recess 210 of housing 200. FIG. 5 shows the volume of first passage 206 with a first cross-section 214, a first vent 212, the volume of the second passage 208 with a second cross-section 216, a second vent 218, the recess 210, and the volume of a pressure sensor mount 220. The pressure sensor 274 may be mounted at the location of the pressure sensor mount 220.

Figure 6:
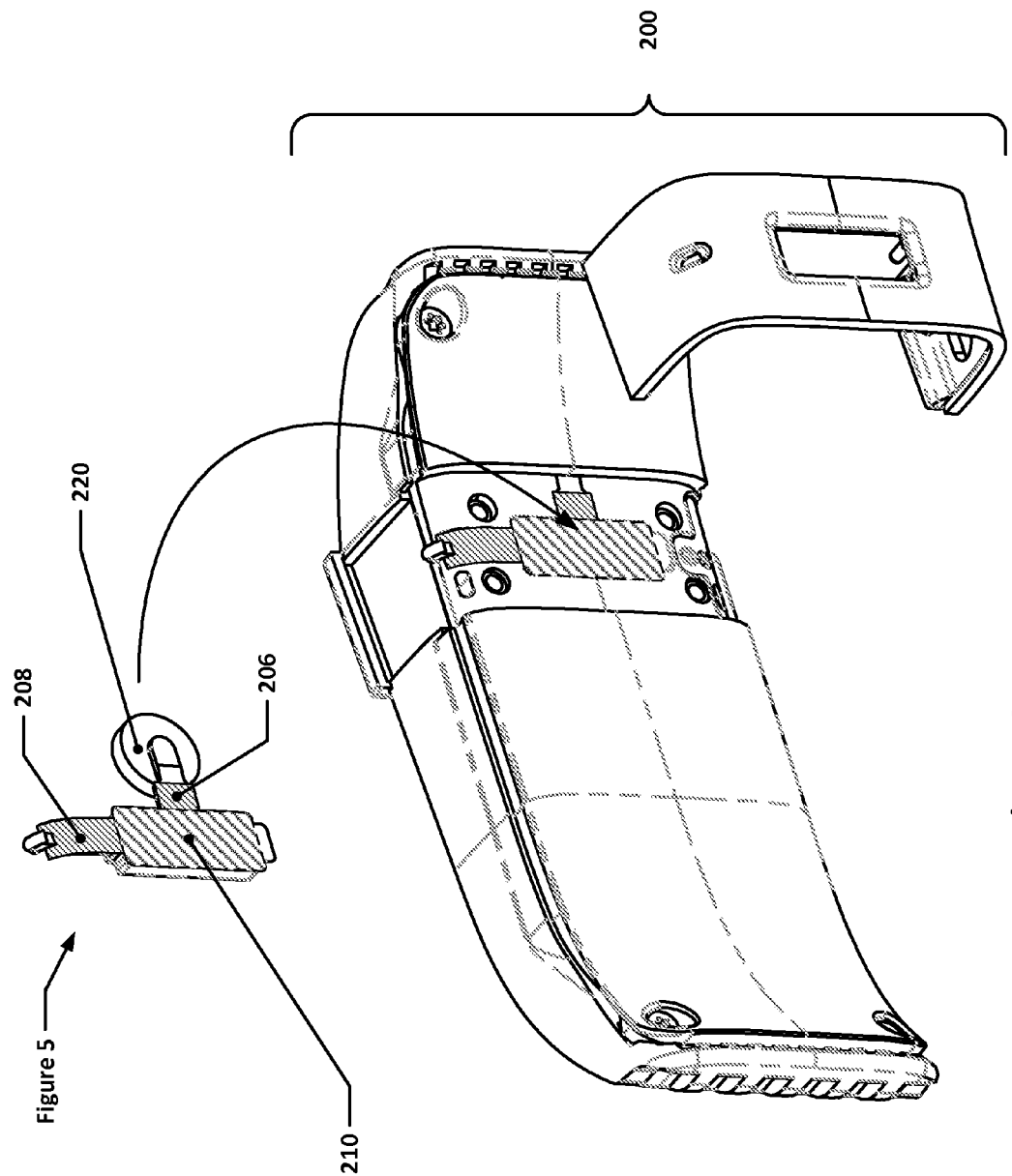
FIG. 6 depicts the location and orientation of the volumetric representation of a first passage, a second passage, and a recess, as shown in FIG. 5, in a housing.

FIG. 6 depicts the location and orientation of the volumetric representation of the first passage 206, second passage 208, and recess 210, shown in FIG. 5, in housing 200 (shown in an exploded view). As discussed above, the cover piece 204 forms part of the boundary of the first passage 206 and the second passage 208, while the housing body 202 forms the remaining boundaries of the first passage 206 and the second passage 208.

Figure 7:
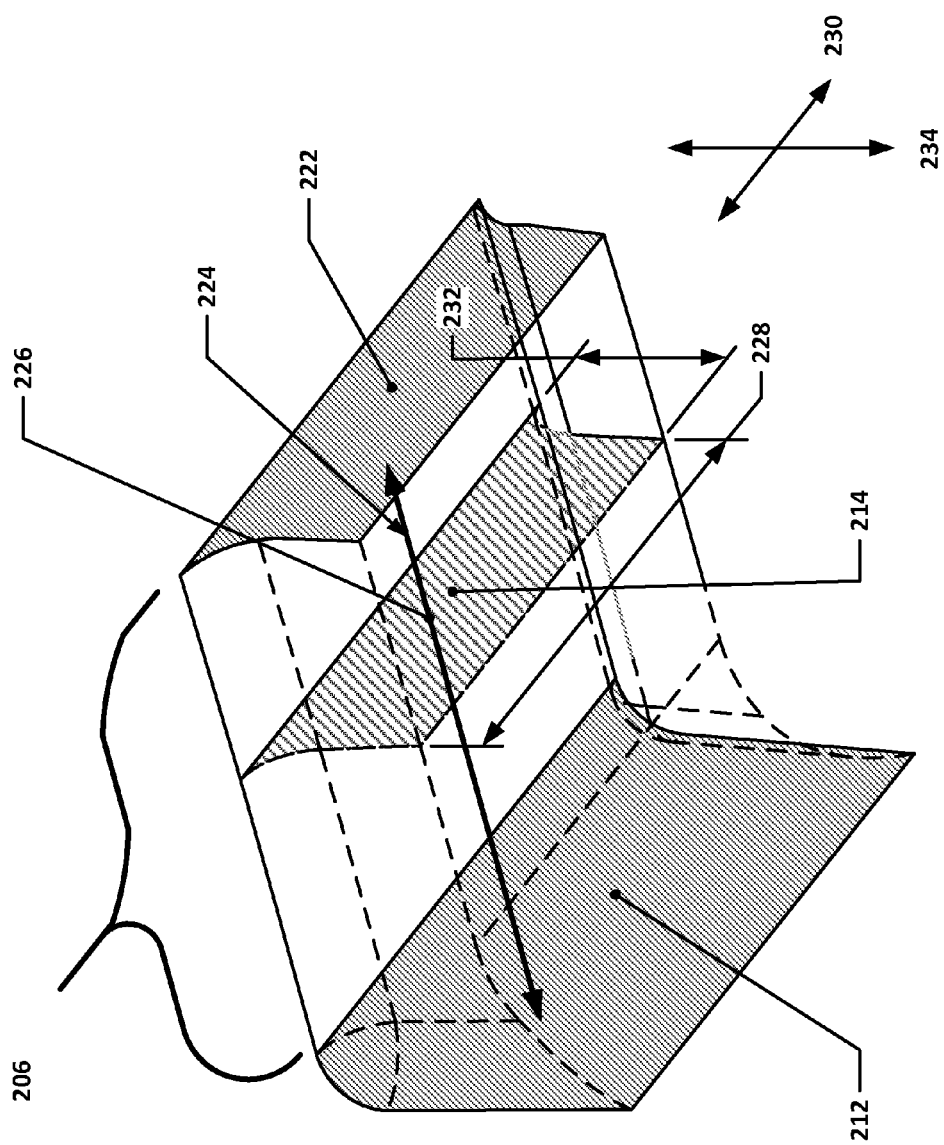
FIG. 7 depicts an isometric view of the volumetric representation of a first passage.

Referring back to FIG. 5, the first passage 206 may have two openings; the first opening may be the vent 212 and the second opening 222 may be at an interface of the first passage 206 with the pressure sensor mount 220. Both such openings are identified with crosshatching. The first passage 206 may provide a first path 224 from the first vent 212 to the pressure sensor mount 220. FIG. 7 depicts an isometric view of the volumetric representation of the first passage 206. As can be seen, the first path 224 is shown as generally linear from the first vent 212 to the second opening 222. In some implementations, the first path 224 may be 2 millimeters or more in length. The first path 224 may span from a point in space of the first vent 212 to a point of space on the second opening 222 and such path may or may not be linear, e.g., straight, and may or may not be a direct path, e.g., it may be curved. For example, the first path 224 may travel through the center of the first passage 206, or be equidistant from opposing surfaces of the passage along its length.

The first passage 206 may allow for air that is external to the housing 200 to travel from the first vent 212 to the pressure sensor. In some implementations, the first passage 206 may be configured to enable the pressure sensor to take a pressure measurement of the air pressure that is external to the housing 200. In some implementations, as can be seen in FIG. 5, the first vent 212 may be located in the recess 210 and the recess 210 may serve as a conduit by which the air that is external to the housing 200 may reach the first passage 206. In some such implementations, when the wearable biometric monitoring device may be worn, the recess may generally be open to the air and/or environment surrounding the housing 200 such that air may travel into the recess 210, into the first vent 212, and then to the pressure sensor by way of the first passage 206.

As identified in FIG. 5, the first passage 206 may also have a first cross-section 214, shown using cross hatching. This first cross-section 214 may be defined by a plane that is perpendicular to the first path 224 and that is located at least at a first point along this first path 224. For instance, referring back to FIG. 7, first cross-section 214 is defined by a plane that is perpendicular to the first path 224 at the first point 226 along the first path 224. In this example, the first cross-section 214 may be the same at other points along the first path 224. This first cross-section 214 may, however, change at other points along the first path 224. For example, in FIG. 7, the first cross-section 214 at the first point 226 is different than the first cross-section 214 that may be located at the location of the first vent 212. Furthermore, first cross-section 214 may differ in size, shape, and/or dimension along at least a portion of the first path 224.

The first cross-section 214 may be measured by a first dimension 228 that is in a first direction 230, and by a second dimension 232 that is in a second direction 234, with the first direction 230 and second direction 234 orthogonal to each other. The first direction 230 and the second direction 234 is not shown in FIG. 5 to avoid undue clutter, but are shown in FIG. 7 and are within the same plane as the first cross-section 214. In some implementations, the first dimension 228 may be at least twice as large as the second dimension 232. For instance, the first dimension 228 may be three times larger than the second dimension 232. During testing, it was observed that a 2:1 ratio or higher in terms of the ratio of the first dimension to the second dimension provided superior performance, and that a 1:1 ratio did not. Accordingly, ratios of the first dimension to the second dimension higher than 1:1 may also provide superior performance.

The first dimension 228 may be measured between two opposite surfaces of the first passage 206. The second dimension 232 may be measured between two other surfaces of the first passage 206 that may also be generally orthogonal to the opposite surfaces used for the measurement of the first dimension 228.

Figure 8:
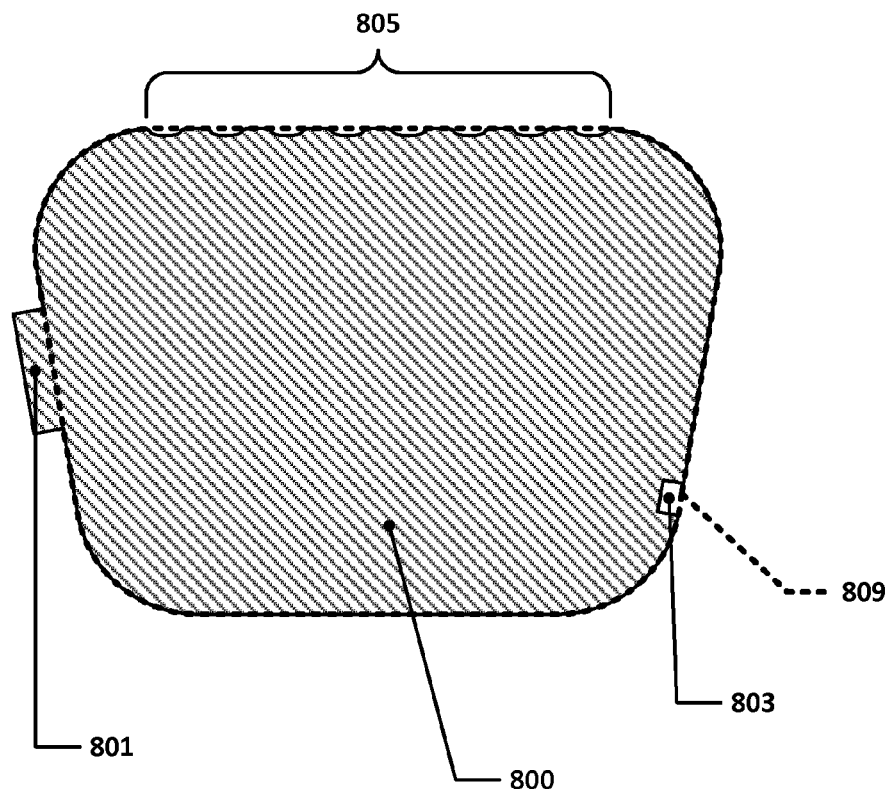
FIG. 8 depicts an example cross-sectional exterior profile of a housing with an overlay of the "average" exterior surface profile for the housing.

In some implementations, the first direction 230 may be tangent to the average exterior surface of the housing 200, which may include the housing body 202 or the cover piece 204. The average exterior surface of the housing 200 may be an average of some or all of the exterior surface of the housing 200 such that, for instance, small variations of the exteriors surface may be minimized. Alternatively, the second direction 234 may be tangent to the average exterior surface of the housing 2, which may include the housing body 202 or the cover piece 204. FIG. 8 depicts an example cross-sectional exterior profile 800 of a housing with an overlay of the "average" exterior surface profile for the housing. For example, the housing exterior profile may include features such as a button 801, a recess 803, and/or surface texturing 805. The "average exterior surface" 809 of the housing, however, may follow the general exterior shape of the housing and may ignore small perturbations in the overall profile of the housing, such as the button 801, the recess 803, and/or the surface texturing 805.

The first path 224, in some implementations, may follow an interior surface of the cover piece 204. The first path 224 may alternatively follow an interior surface of the housing body 202. In some such implementations, the first path 224 may have a curved shape. For example, the first path 224 may follow a 2-dimensional curve in a plane that is normal to the first direction 230 or that is normal to the second direction 234. In some implementations, the first path 224 may be elongated and/or straight such that it does not have sharp bends or angles or corners in which water may get stuck.

As discussed earlier, the present inventors determined that a significant increase in the data quality of the pressure sensor is achieved when the passage, e.g., the first and/or second passage, that allows air external to the wearable biometric monitoring device to travel from the first vent to the pressure sensor has a cross-section with a minimum aspect ratio. More specifically, in some implementations, the present inventors have determined that using an aspect ratio of at least 2:1 for a passage cross-section may provide a significant increase in the data quality of the pressure sensor. In some experiments, the present inventors discovered that when water entered a passage with a cross-section that had at least a 2:1 ratio, the pressure sensor data was significantly less noisy, which indicated that water in the passage was causing substantially less, or causing no, pressure fluctuation in the passage as compared with passages having other cross-sectional characteristics.

The present inventors also discovered that, in some implementations, there may be a minimum effective length of the first dimension 228 and/or the second dimension 232 such that at some lengths, the aforementioned benefits did not occur despite having at least a 2:1 ratio. For instance, in one implementation, the present inventors found that using a first dimension 228 of approximately 1 millimeter and a second dimension 232 of about 0.5 millimeter did not provide the above benefits, despite having a 2:1 ratio. However, in some implementations, a first dimension greater than about 1 millimeter may provide the above benefits. The present inventors also found that in some implementations, the first dimension 228 may have an effective length between about 2 millimeters and 4 millimeters, while the second dimension 232 may have an effective length between about 0.3 millimeters and 1 millimeter. In some such implementations, if the first dimension 228 is at least 2 mm and the first cross-section 214 has at least a 2:1 ratio, then the benefits described above may be realized for the first passage 206.

It is to be understood that the passages discussed herein, e.g., the first passage or the second passage, do not necessarily need to be rectangular in cross-section, but may have a variety of shapes that may still be thought of as generally rectangular. FIGS. 9 through 16 provide examples of various types of cross-sectional shapes for a first passage that may be thought of as generally rectangular despite not being strictly rectangular (these shapes may also be applicable to second passages, or other passages). For ease of reference, FIGS. 9 through 16 may each include a diagonal-hatched region that represents a 2:1 rectangular area.

Figure 9:
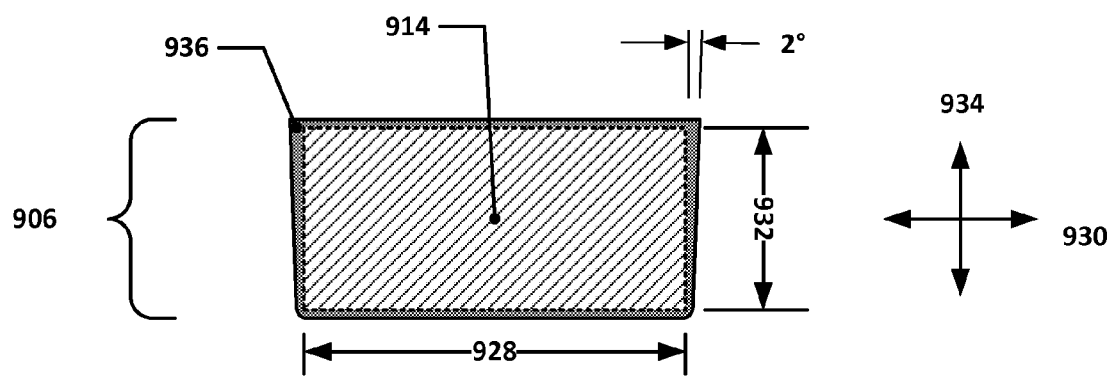
FIGS. 9 through 16 provide examples of various types of cross-sectional shapes for a first passage that may be thought of as generally rectangular despite not being strictly rectangular.

FIG. 9 depicts an example passage 936 with a non-square geometry and a region 914 having a first dimension 928 and a second dimension 932 that have a 2:1 ratio. Here, the passage 936 includes two walls which are at approximately 2° angles from normal and two corners which are internally rounded. Despite this non-rectangular geometry, the cross-section of the passage 936 may still be described as being generally rectangular and having at least a 2:1 ratio of the first dimension 928 to the second dimension 932.

In recognition of the wide variety of different cross-sections that may be used for a passage, in some implementations, it is to be understood that the entire cross-sectional area of the passage need not have the characteristics of a 2:1 or greater first dimension/second dimension ratio. In such cases, it may be sufficient for only 90% or 95% of the passage cross-sectional area to exhibit such characteristics.

Figure 10:
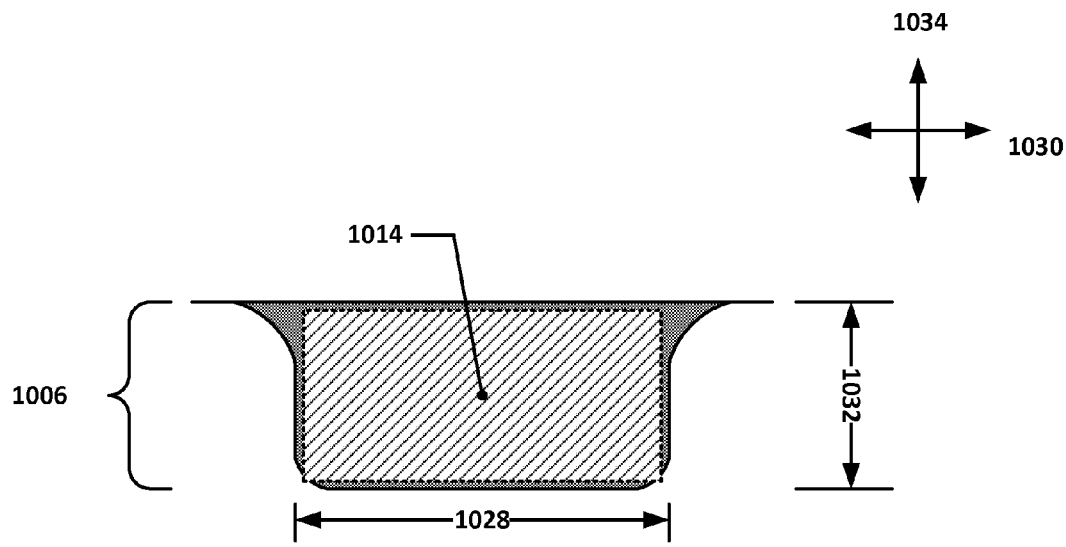

FIG. 10 depicts a passage 1006. As can be seen, the passage 1006 has a geometry that is not precisely rectangular in shape, but is generally rectangular with various internal fillets and curvatures. Despite the geometry of the passage 1006 in FIG. 10, the first dimension 1028 is still at least twice as large as the second dimension 1032—both when measured from the major interior surfaces of the passage 1006 and when measured from the widest portion of the passage 1006. For reference, the rectangular region 1014 depicts a 2:1 aspect ratio rectangle.

Figure 11:
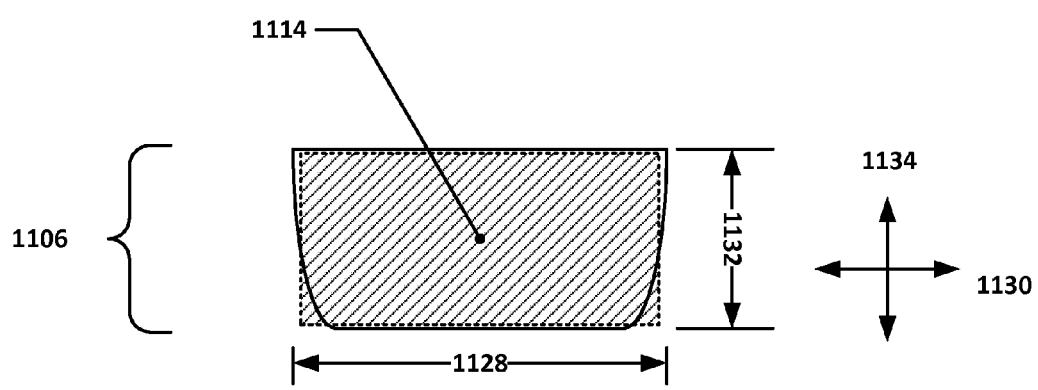

FIG. 11 depicts an example passage 1106 that has gently-curving side-walls. For ease of reference, a region 1114 is shown that has a first dimension 1128 in a first direction 1130 that is twice as large as a second dimension 1132 in a second direction 1134. As can be seen, if the first dimension 1128 of the passage cross-section 1136 is evaluated using the bottom of the passage, the ratio of the first dimension 1128 to the second dimension 1132 of the passage 1106 would be slightly less than 2:1. However, if the first dimension 1128 of the passage 1106 is evaluated using the top of the passage 1106, then the ratio of the first dimension 1128 to the second dimension 1132 would be slightly greater than 2:1. Moreover, approximately 95% of the passage cross-sectional area still falls within the region 1114, and the passage would thus still be viewed as having a cross-section with a first dimension 1128 that is at least twice as large as the second dimension 1132.

Figure 12:
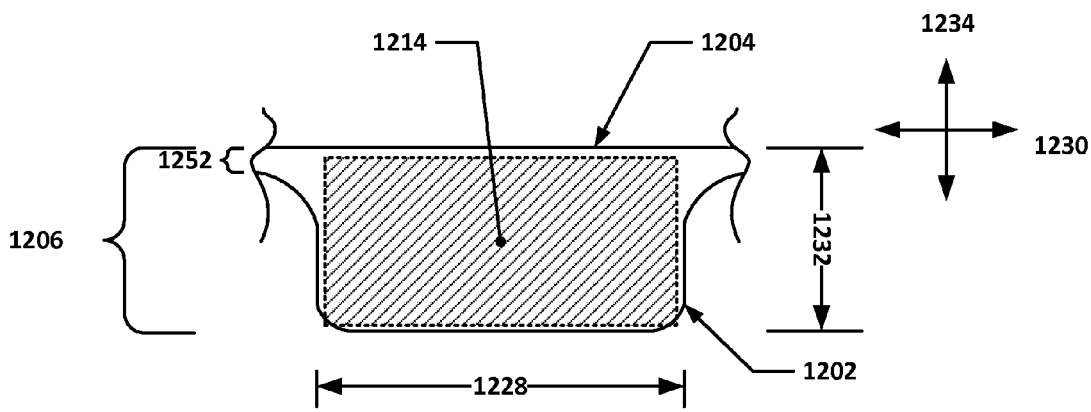

FIG. 12 depicts another example passage 1206. In this example, which may be representative of some implementations in which a cover piece is used, there may be a small gap 1252, e.g., tenths or hundredths of a millimeter, between the cover piece 1204 and the housing body 1202; such a gap may be due to assembly fit, or may be a result of a manufacturing process. It is to be understood that such small assembly gaps are not considered part of the cross-sectional area of the passage, and should not be viewed as contributing to the ratio of the first dimension 1228 (in direction 1230) to the second dimension 1232 (in direction 1234). Thus, for example, the cross-sectional area of the depicted passage 1206 may be thought of as generally being coextensive with the region 1214, which has a 2:1 ratio.

Figure 13:
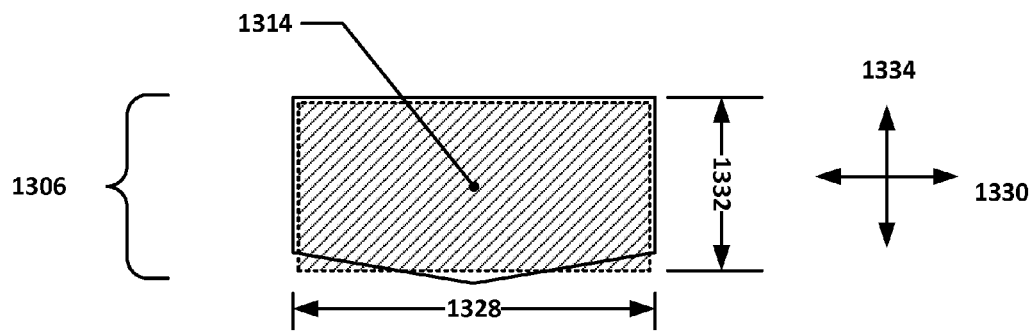

FIG. 13 depicts an example passage 1306 with a five-sided boundary in the shape of a rectangle with a chevron-shaped floor. In this example, the bottom of the passage 1306 protrudes slightly out of a region 1314, which has a first dimension 1328 along a first direction 1330 that is twice as large as a second dimension 1332 along a second direction 1334. However, since at least 95% of the cross-sectional area of the passage 1306 would fall within the region 1314, the passage 1306 would still be viewed as having a first dimension 1328 that is at least twice as large as a second dimension 1332.

Figure 14:
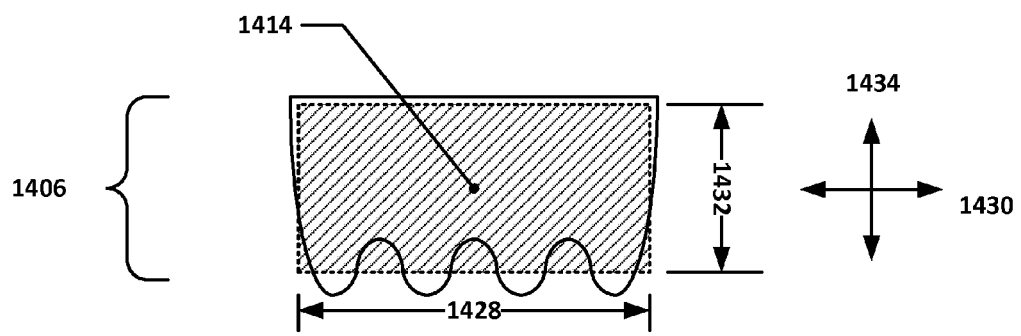

FIG. 14 depicts an example passage 1406 with a corrugated, or wavy, bottom. Such a passage may still be viewed as have a first dimension 1428 along a first direction 1430 that is at least twice as large as a second dimension 1432 along a second direction 1434. In this case, the second dimension 1432 of the passage 1406 may be evaluated with respect to the "average" surface defined by the wavy floor, e.g., a surface that generally aligns with the bottom of the region 1414. When evaluated in this manner, at least 95% of the cross-section of the passage 1406 may still be seen to have a first dimension 1428 in the first direction 1430 that is at least twice as large as the second dimension 1432 in the second direction 1434.

Figure 15:
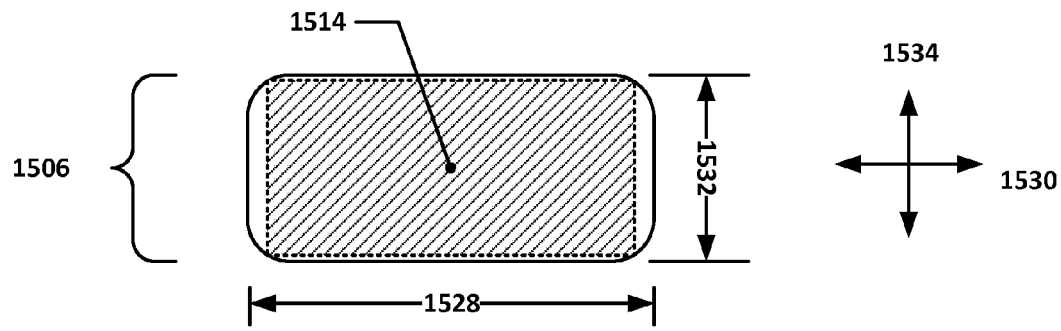

FIG. 15 depicts an example passage 1506 that has a rectangular cross-section with filleted or internally-rounded corners. In this case, the passage 1506 has a first dimension 1528 along a first direction 1530 that is at least twice as large as a second dimension 1532 along a second direction 1534.

Figure 16:
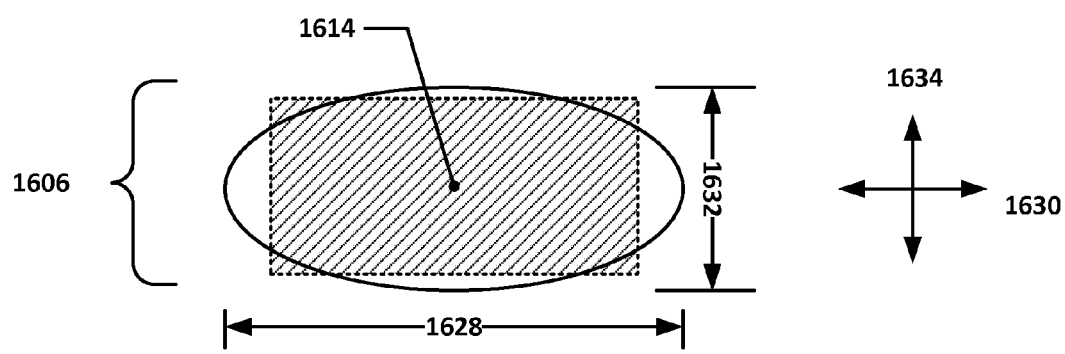

FIG. 16 depicts an example passage 1606 with an elliptical cross-section. While the passage 1606 has an elliptical cross-section, it may also be described as having a cross-sectional area that has a first dimension 1628 that is at least twice as large as a second dimension 1632. While the passage 1606 may still provide an increased level of pressure sensor data quality due to this ratio, the absence of "corners" in the elliptical cross-section may result in lower data quality as compared with other passages having similar aspect ratios but having a more "rectangular" format. Moisture droplets that enter a passage may be drawn towards any corners that are present in the passage. In a 2:1 aspect ratio or higher passage, for example, this may encourage any moisture droplets in the passage to collect near the "short" sides of the passage, thus pulling the moisture droplets away from the center of the "long" sides of the passage. This helps promote a clear pathway through the passage.

In some implementations, the first cross-section 214 may be the same, e.g., with the same first dimension 228 and same second dimension 232, for at least 90% of the length of the first path 224. In some such implementations, the first path may be at least 2 mm long in length.

Figure 17:
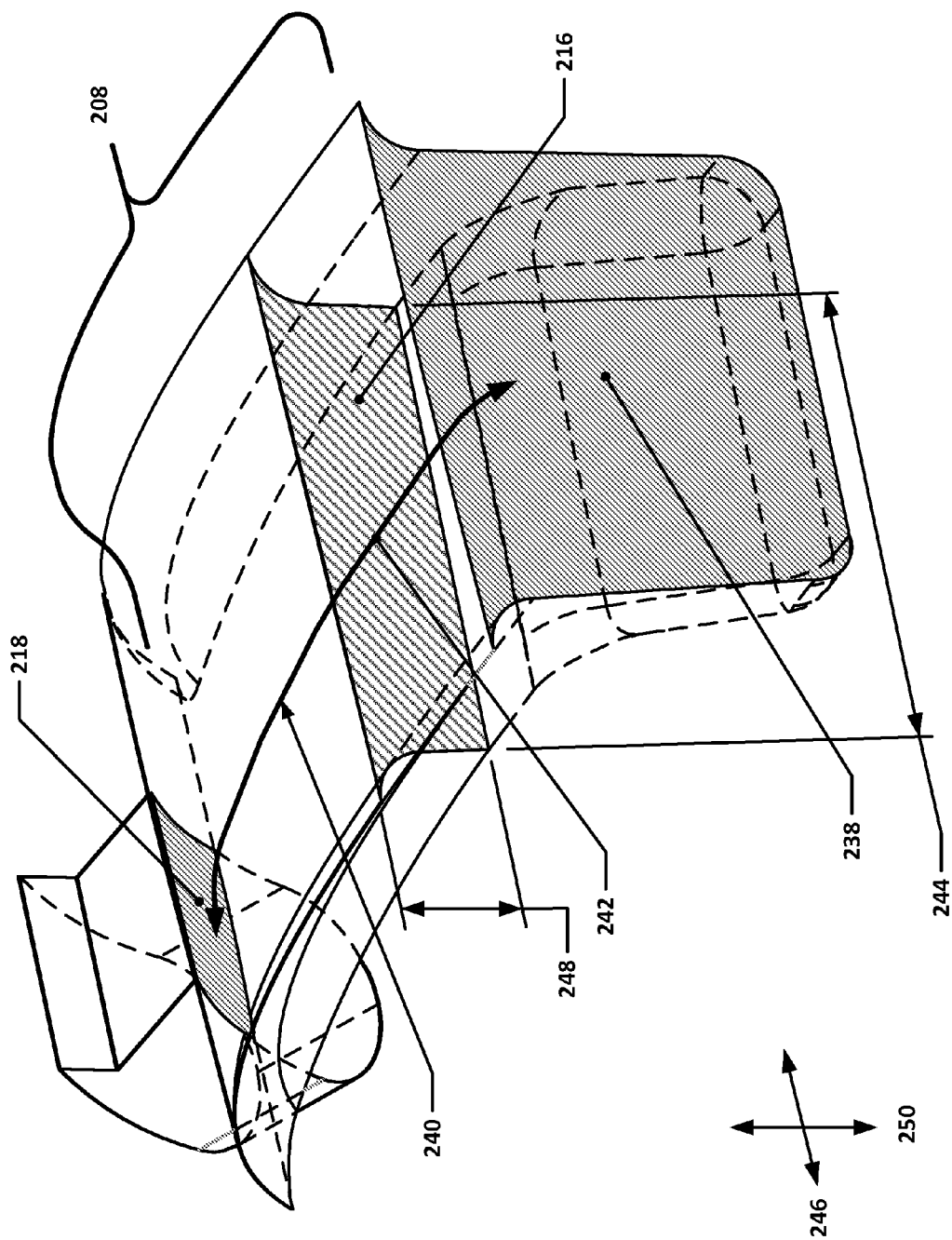
FIG. 17 depicts an isometric view of the volumetric representation of a second passage.

Some aspects of the second passage 208 will now be discussed. The second passage 208 can be seen in FIG. 4, FIG. 5, and FIG. 17. FIG. 17 depicts an isometric view of the volumetric representation of the second passage 208. As stated above and seen in FIGS. 5 and 17, the second passage 208 includes the second cross-section 216 and the second vent 218. Similar to the first passage 206, the second passage 208 may have two openings; the first opening may be the second vent 218 and a second opening 238 may be the interface, e.g., connection, between the second passage 208 and the recess 210 of the housing body 202. Both openings are identified with cross-hatching in FIG. 5.

The second passage 208 may provide a second path 240 from the second vent 218 to the second passage opening 238 and/or to the recess 210. This second path 240 may span from one point in space of the second vent 218 to one point of space on the second passage opening 238 and such path may or may not be linear, e.g., straight, and may or may not be a direct path, e.g., it may be circuitous. As can be seen in FIG. 17 (which is similar to FIG. 7 in that it depicts a sub-portion of the volumes depicted in FIG. 5), the second passage 208 may have a curved shape and the second path 240 may be a curvilinear path from the second vent 218 to the second passage opening 238. The second path 240 may follow a 2-dimensional curve in a plane that is normal to a third direction 246 or normal to the first direction 230. In some implementations, the second path 240 may follow an interior surface of the cover piece 204. In some implementations, the first path 224 may alternatively follow an interior surface of the housing body 202. The second passage 208 may also, at least in part, be defined by surfaces of the housing body 202 and the cover piece 204 when the cover piece 204 is assembled to the housing body 202.

The second passage 208 may allow for air that is external to the housing 200 to travel from the second vent 218 to the recess 210. In some implementations, the second passage 208 may be configured to enable the pressure sensor to take a pressure measurement of the air pressure that is external to the housing 200. In some such implementations, this may occur when the biometric monitoring device is worn and a seal is created between an area of the housing 200 immediately surrounding the recess 210 and, for example, the wearer's skin. In such a situation, the only pathway for air into the recess 210, and thus to the first passage 206, may be through the second passage 208. The air may travel through the second vent 218, into and through the second passage 208, through the second passage opening 238 into the recess 210. The air may then continue to travel through the first vent 212, through the first passage 206, and to the pressure sensor.

The second vent 218 may be located on an external surface of the housing 200. In some such implementations, the second vent 218 may be located on an external surface of the housing in a location that is not adjacent to a user's skin when the biometric monitoring device is worn. The second vent 218 may also be located such that it does not face towards a user's skin when the biometric monitoring device is worn. As discussed above, when the second vent 218 is configured in such a location, a user's skin is less likely to interact with the second vent 218 and cause pressure fluctuations in passage to the pressure sensor, thereby leading to higher-quality pressure sensor readings.

Figure 18:
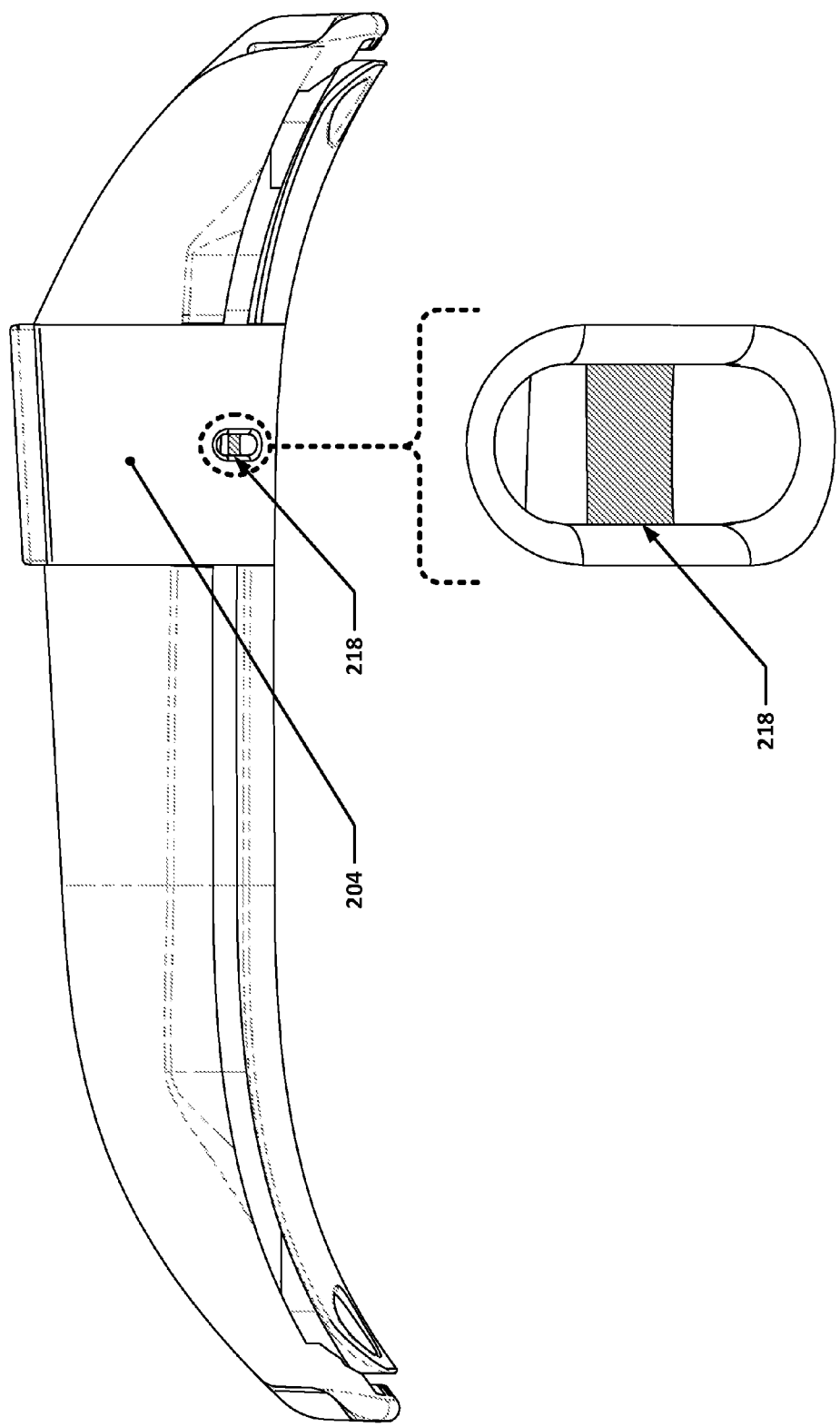
FIG. 18 depicts a side view of the housing of FIG. 2 and a close-up view of the second vent and cover piece.

In some implementations, the second vent 218 may be located on the cover piece 204 of the housing 200. FIG. 18 depicts a side view of the housing 200 of FIG. 2 and a close-up view of the second vent 218 and cover piece 204. In FIG. 18, the second vent 218 can be seen in cross-hatching; this cross-hatched portion is the portion of the second vent that is exposed to the ambient environment external to the housing 200. In some implementations, the second vent 218 may have a different, shape, and/or size than that depicted in FIG. 18. As shown in FIG. 18, the second vent 218 is located on the cover piece 204 such that when the biometric monitoring device is worn, the second vent 218 is not adjacent to a user's skin and does not face towards a user's skin, but is rather 1 mm-2 mm above the person's skin.

As identified in FIGS. 5 and 17, the second passage 208 may also have a second cross-section 216, also shown using cross-hatching. This second cross-section 216, may be defined by a plane that is perpendicular to the second path 240 and that is located at least at a second point 242 along this second path 240, similar to the first cross-section 214 with respect to the first path 224. For example, FIG. 17 shows that the second cross-section 216 is defined by a plane that is perpendicular to the second path 240 at a second point 242 along the second path 240. In this instance, the second cross-section 216 may be the same at other points along the second path 240, but may, however, change at other points along the second path 240, such as at the location of the second passage opening 238.

The second cross-section may be measured by a third dimension 244 that is in the third direction 246, and by a fourth dimension 248 that is in a fourth direction 250, with the third direction 246 and fourth direction 250 orthogonal to each other. The third direction 246 and the fourth direction 250, which are shown in FIG. 17 (but not in FIG. 5 to avoid undue clutter), are within the same plane as the second cross-section 216. In some implementations, the third dimension 244 may be at least twice as large as the fourth dimension 248. For instance, the third dimension 244 may be three times larger than the fourth dimension 248. Like with the first passage 206, the third dimension 244 may be measured between two opposite surfaces of the second passage 208.

As stated above, the present inventors determined that a significant increase in the data quality of the pressure sensor is achieved when the passages through which the air flows within the housing, including the second passage 208, have a cross-section with a minimum aspect ratio, which may specifically include an aspect ratio of at least 2:1 for the passage cross-section. Accordingly, it is to be understood that all of the above discussion, including the discussion of FIGS. 9 through 16, applies in its entirety to the second cross-section 216. It is to be understood that, with respect to the second cross-section 216, the third dimension may be analogous to the first dimension 228 and the fourth dimension may be analogous to the second dimension 232.

Figure 19:
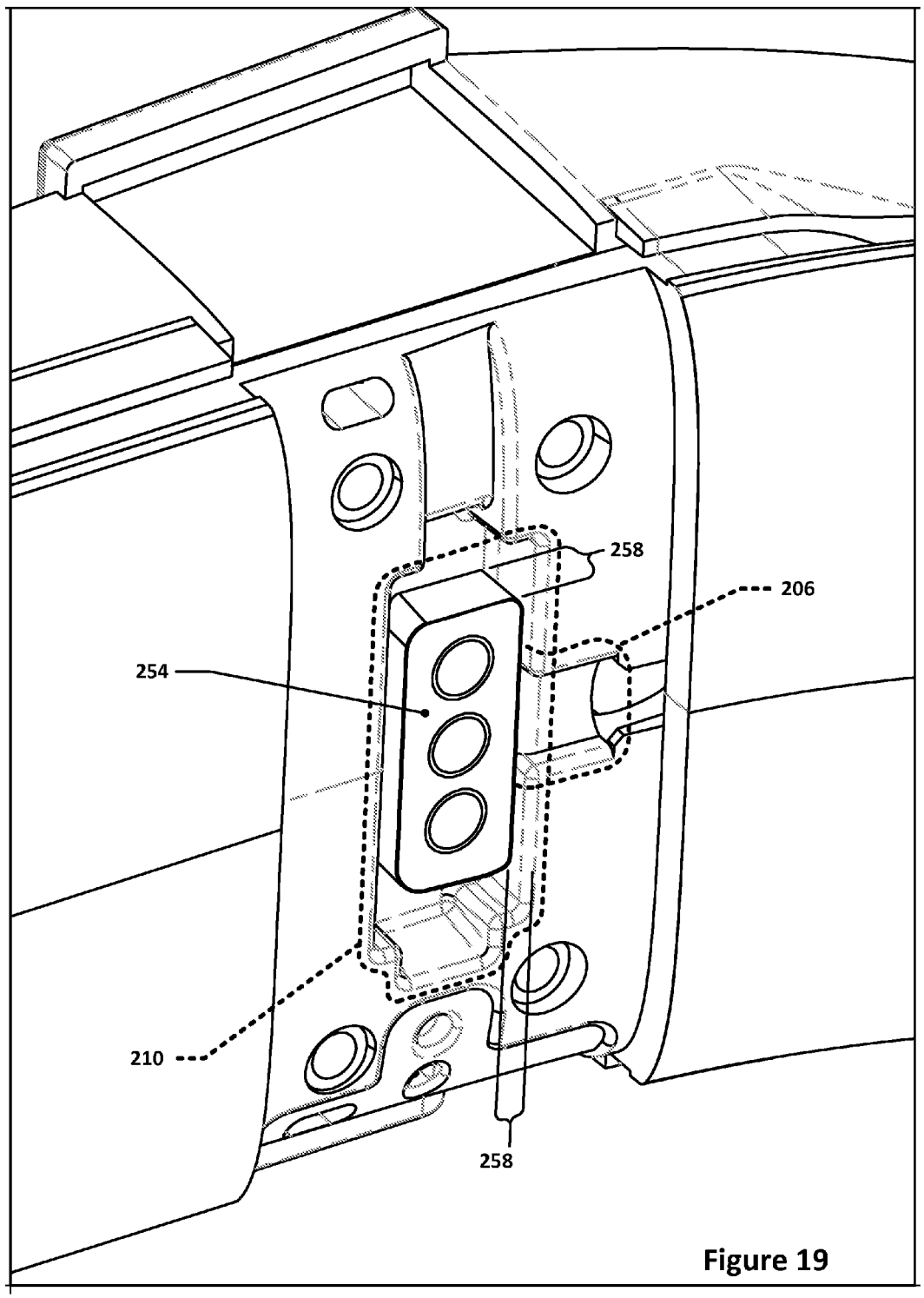
FIG. 19 depicts a close-up of a housing body similar to that shown in FIG. 4, but includes a protrusion in the recess.

In some implementations, the recess 210 may include a protrusion 254. FIG. 19 depicts a close-up of housing body 202 similar to that shown in FIG. 4, but includes a protrusion 254 in the recess 210; such a protrusion may be present, for example, in order to accommodate a particular type of electrical connector. As can be seen, this protrusion 254 may produce a gap 256 that exists between the side walls of the recess 210 and the side walls of the protrusion 254. The gap 256 may be an offset distance between the side walls of the recess 210 and the side walls of the protrusion 254. In some implementations the offset distance may be uniform while in some other implementations, the offset distance may not be uniform between the side walls of the protrusion 254 and the side walls of the recess 210. The gap 256 may also have a gap depth 258 which may be defined by a height of the protrusion 254 and/or by a depth of the recess 210. In some implementations, the gap depth 258 may be at least twice as large as the width of the gap 256, such that when the recess is closed off, such as by a wearer's skin, the gap forms, in effect, another passage having a first dimension (in this case, the gap depth) that is at least twice as large as a second dimension (in this case, the offset distance). In some implementations, the gap-depth-to-gap-width ratio may be 1.5:1 or higher.

Figure 20:
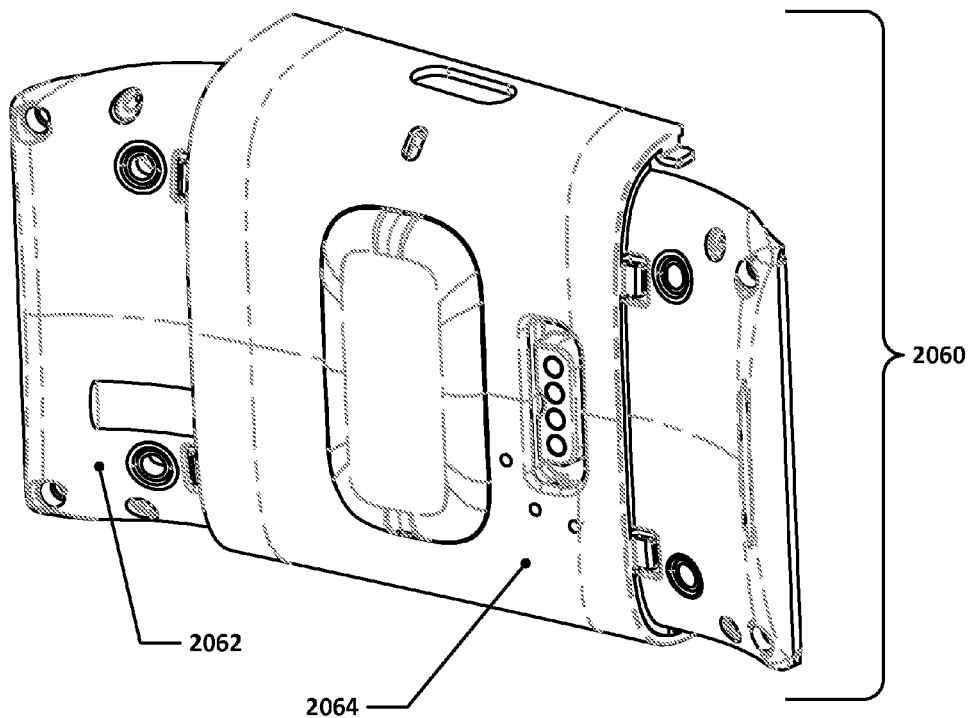
FIG. 20 depicts an isometric view of a housing for a second example wearable biometric monitoring device.
Figure 21:
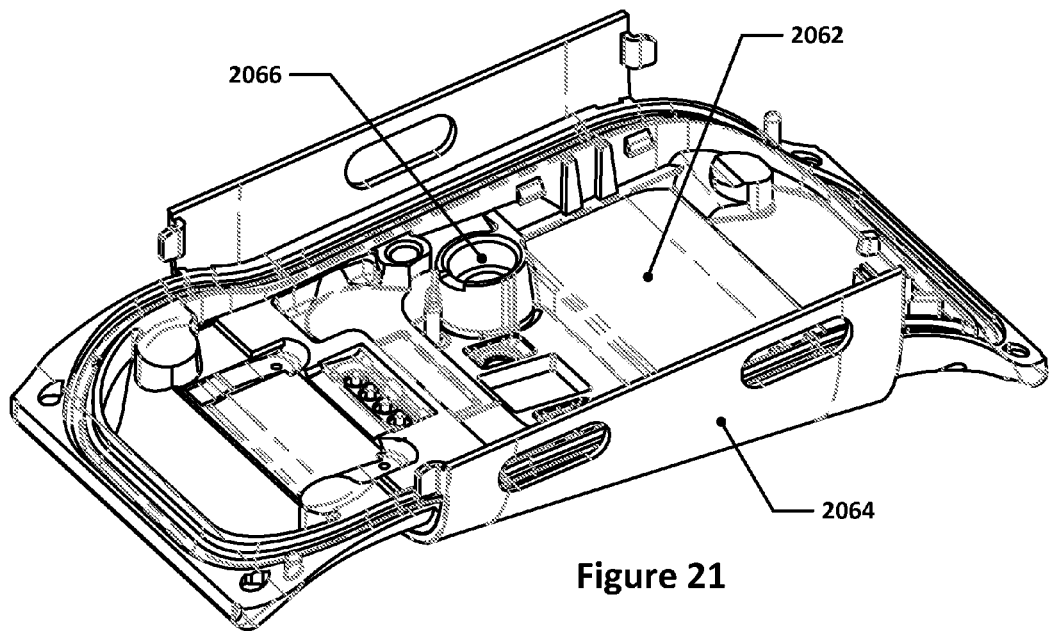
FIG. 21 depicts a different isometric view of the housing in FIG. 20.

A second example implementation of the wearable biometric monitoring device will now be discussed. FIG. 20 depicts an isometric view of a housing 2060 for a second example wearable biometric monitoring device (the housing 2060 may have straps affixed to it, as with the biometric monitoring device of FIG. 1). The housing 2060 may include a housing body 2062 and a cover piece 2064. FIG. 21 depicts a different isometric view of the housing 2060 in FIG. 20. Similar to housing 200, in FIG. 21 the housing 2060 includes a pressure sensor mount and/or pressure sensor plenum volume 2066.

Figure 22:
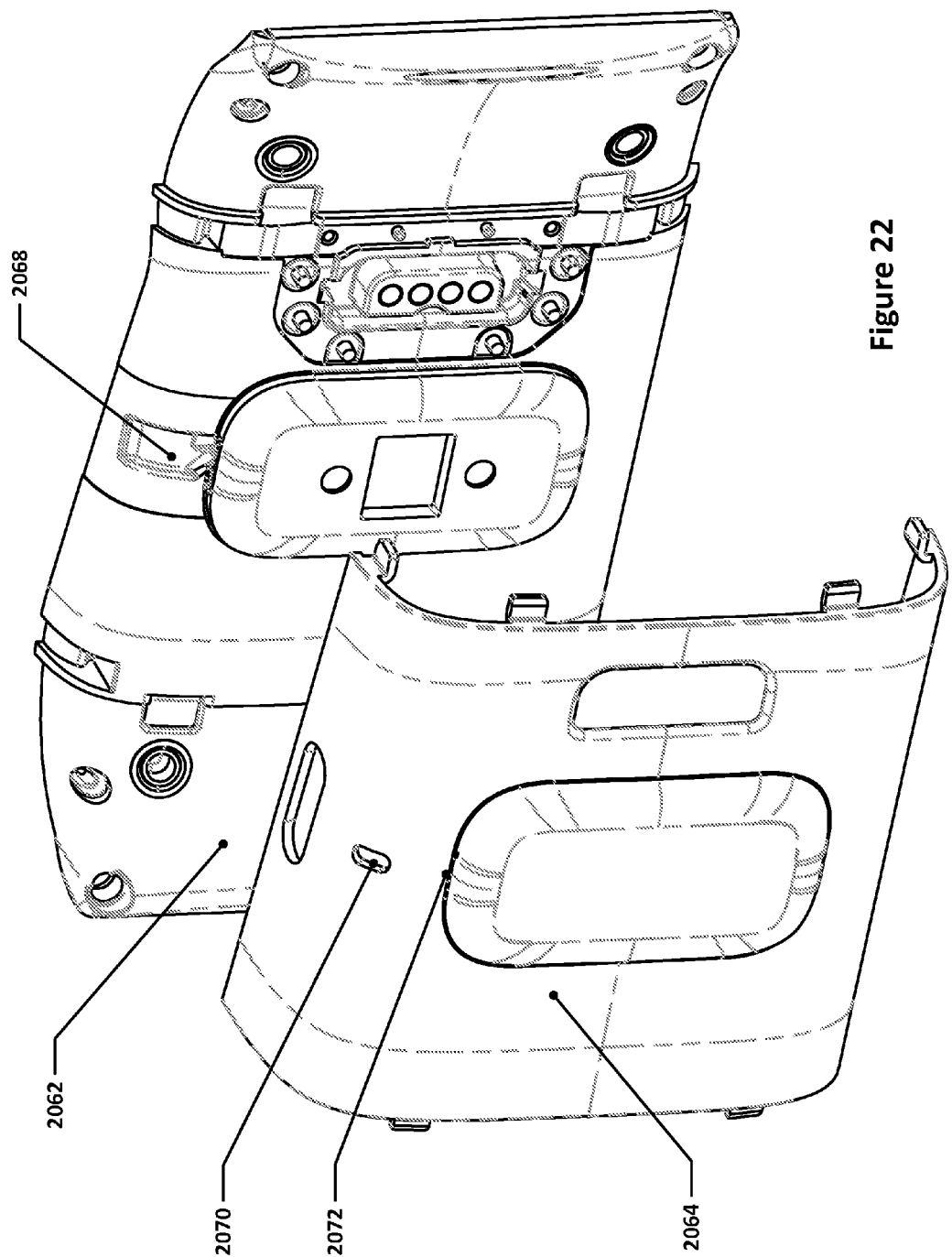
FIG. 22 depicts a partially exploded isometric view of the housing in FIG. 21.

FIG. 22 depicts a partially exploded isometric view of the housing 2060. As can be seen, the housing body 2062 is oriented in a similar fashion to FIG. 20, but the cover piece 2064 has been removed from the housing body 2062. A first passage 2068 is included in the housing body 2062 and as discussed below, the first passage 2068 may allow air to travel from a vent to a pressure sensor (not shown) in the pressure sensor mount 2066, and may be configured similar to the first passage 206 discussed above. In some implementations, the wearable biometric monitoring device may only have one pressure sensor passage, e.g., the first passage 2068, that allows air external to the biometric monitoring device to travel to the pressure sensor. In order to achieve the benefits described above, the first passage 2068 may have one or more vents. As shown in FIG. 22, the cover piece 2064 includes a first vent 2070 and a second vent 2072 (the second vent 2072 is a very thin slit that exists at the location indicated), both of which may be connected to the first passage 2068 in order to allow air external to the housing 2060 to pass through the first vent 2070 and/or second vent 2072, travel into and through the first passage 2068, and to the pressure sensor (not shown) at the pressure sensor mount 2066.

The first vent 2070 may be placed at a first location on an outer surface of the housing 2060 and the second vent 2072 may be located at a second location on the outer surface of the housing 2060. For instance, in FIG. 22 the first vent 2070 is located at a first location on the cover piece 2064, the second vent 2072 is placed at a second location on the cover piece 2064, and the first vent 2070 and the second vent 2072 are at different locations. In some implementations, the first vent 2070 and/or second vent 2072 may be placed on other locations of the housing 2060 including, but not limited to, the housing body 2062.

Figure 23:
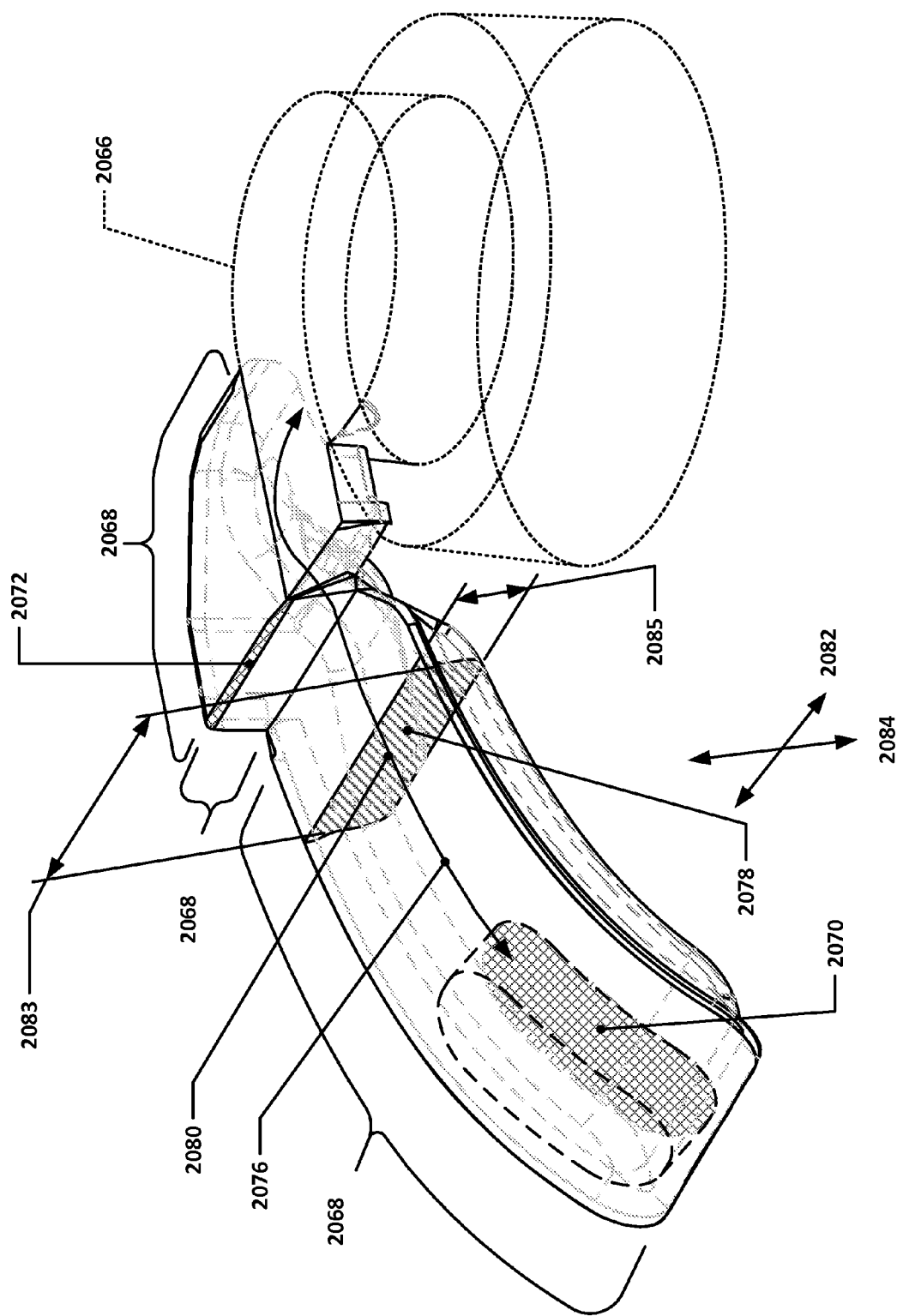
FIG. 23 depicts the volumetric representation of the first passage in the housing for the second example implementation of the wearable biometric monitoring device.

FIG. 23 depicts the volumetric representation of the first passage 2068 in the housing 2060 for the second example implementation of the wearable biometric monitoring device. Similar to FIG. 5, FIG. 23 shows the "negative space", or the volume, of the first passage 2068 within the housing 2060. The first vent 2070 and the second vent 2072 are identified with diamond hatching and are located at different points along the first passage 2068 such that each vent enables air to enter into the first passage 2068 and travel through the first passage 2068 to the pressure sensor. The first vent 2070 and/or second vent 2072 may be located along the first passage 2068 such that if one vent is obstructed, e.g., by the skin of a user, then the other vent may enable air to enter into the first passage 2068. Additionally, the first vent 2070 and/or the second vent 2072 may be located along the first passage 2068 so that they are not facing into a person's skin when the wearable biometric device is worn. For example, the first vent 2070 depicted in FIG. 22 is located such that it is not facing a user's skin when the device is worn.

The first passage 2068 may provide a first path 2076 from the first vent 2070 to the pressure sensor and from the second vent 2072 to the pressure sensor. As stated above, because both vents are located on the first passage 2068, a single, common first path 2076 is provided to the pressure sensor. FIG. 23 shows an example first path 2076 for the first passage 2068 which may indicate the general direction air may travel from the first vent 2070 and/or the second vent 2072 to the pressure sensor. In some implementations, the first vent 2070 may extend through the cover piece 2064 and/or the housing body 2062 to the first passage 2068. Likewise, the second vent 2072 may also extend through the cover piece 2064 and/or the housing body 2062 to the first passage 2068. In some implementations, the second vent may be formed between one or more surfaces of the housing body 2062 and one or more surfaces of the cover piece 2064.

The first passage 2068 may have a first cross-section 2078 as shown in FIG. 23. Like the discussion above regarding the first cross-section 214, the first cross-section 2078 may be configured in a similar manner and the discussions applicable to the first cross-section 214, including, but not limited to the discussions regarding FIGS. 9 through 16, are applicable to this second example implementation of the wearable biometric monitoring device as well. For instance, first cross-section 2078 may be defined by a plane that is perpendicular to the first path 2076 that is located at a first point 2080 along the first path 2076. The first cross-section 2078 may be the same at other points along the first path 2076 and may also be different at other points along the first path 2076. Furthermore, first cross-section 2078 may differ in size, shape, and/or dimension along at least a portion of the first path 2076.

Similar to the first cross-section 214, the first cross-section 2078 may be measured by a first dimension 2083 that is in a first direction 2082, and by a second dimension 2085 that is in a second direction 2084, with the first direction 2082 and second direction 2084 orthogonal to each other as shown in FIG. 23. In some implementations, the first dimension may be at least twice as large as the second dimension, and in some implementations, the first dimension may be at least three times as large as the second dimension.

The first dimension 2083 may be measured between two opposite surfaces of the first passage 2068. The second dimension 2085 which is in the second direction 2084 that is orthogonal to the first direction 2082, may be measured between two other opposing surfaces of the first passage 2068. The first dimension 2083 and the second dimension 2085 may also be measured between points located anywhere in the plane of the first cross-section 2078.

In some implementations, as depicted in FIG. 23, the first passage 2068 may have a curved, non-linear, and/or non-uniform shape. The first passage 2068 may also, at least in part, be defined by surfaces of the housing body 2062 and/or the cover piece 2064 when the cover piece 2064 is assembled to the housing body 2062. The first passage 2068 in FIG. 23 is defined in such a way. The first path 2076 may follow a 2-dimensional curve in a plane that is normal to the first direction 2082, although in some implementations, the first path 2076 may follow a three-dimensional path, such as in the depicted implementation. In some implementations, the first path 2076 may follow an interior surface of the cover piece 2064. In some implementations, the first path 2076 may alternatively follow an interior surface of the housing body 2062.

In addition to the use of passages having characteristics as described above, the present inventors also determined that passages having characteristics other than those discussed above may also be used in certain configurations to achieve beneficial results with respect to reducing pressure sensor signal noise. In these alternative implementations, the cross-sections of the passages may deviate from having a first dimension that is at least twice as large as a second dimension. In fact, the passages in these alternative implementations may utilize passages that have 1:1 aspect ratios, e.g., circular or square cross-section passages.

Figure 24:
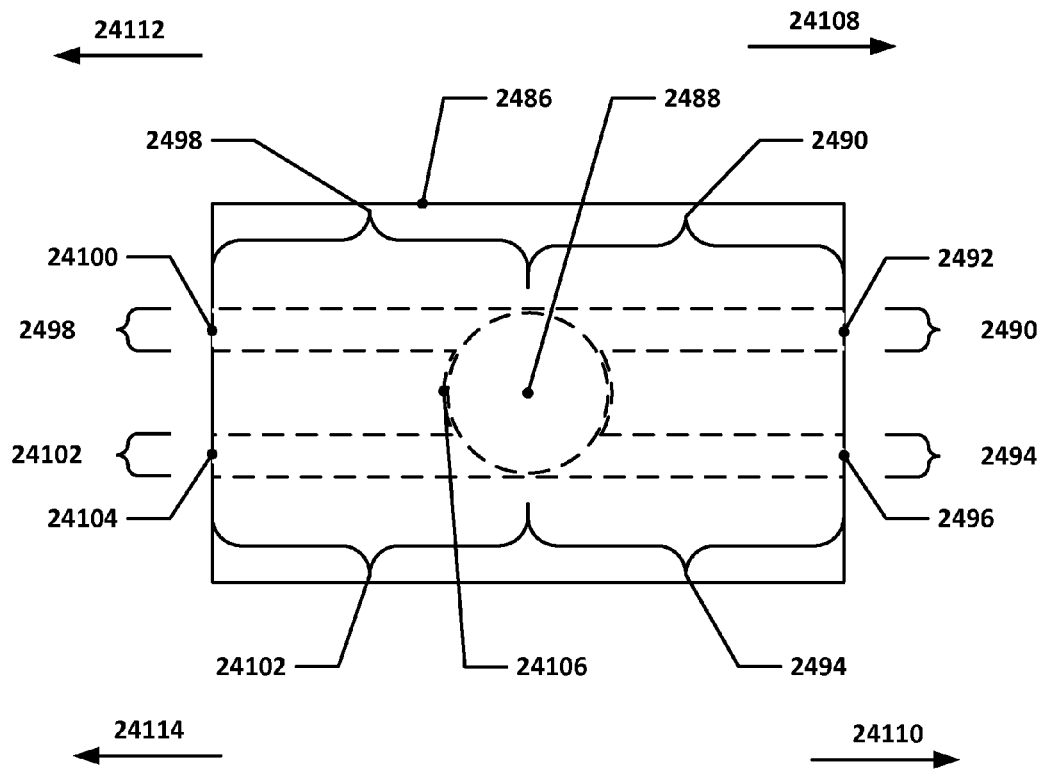
FIG. 24 depicts a general example configuration of a wearable biometric monitoring device featuring an alternative passage design.
Figure 25:
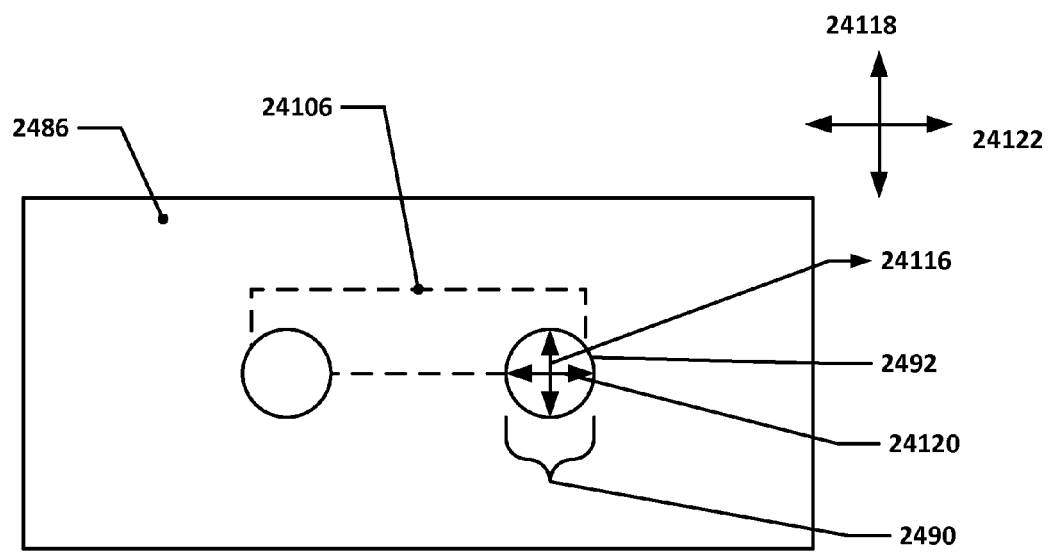
FIG. 25 depicts another view of the general example configuration of the alternative example wearable biometric monitoring device of FIG. 24.

FIG. 24 depicts a general example configuration of a wearable biometric monitoring device featuring an alternative passage design. A representational box indicating a housing 2486 is shown that includes a pressure sensor 2488, a first passage 2490 with a first vent 2492, a second passage 2494 with a second vent 2496, a third passage 2498 with a third vent 24100, and a fourth passage 24102 with a fourth vent 24104. The pressure sensor 2488 is located in or adjacent to a pressure sensor plenum volume 24106 that is in fluidic communication with the pressure sensor such that a fluid, e.g., air, may travel between the pressure sensor plenum volume 24106 and the pressure sensor 2488.

FIG. 24 also shows the general directions of the passages in housing 2486. The first passage 2490 may extend away from the pressure sensor plenum volume 24106 in a first direction 24108, the second passage 2494 may extend away from the pressure sensor plenum volume 24106 in a second direction 24110, the third passage 2498 may extend away from the pressure sensor plenum volume 24106 in a third direction 24112, and the fourth passage 24102 may extend away from the pressure sensor plenum volume 24106 in a fourth direction 24114. The first passage 2490 and the second passage 2494 may or may not have the same orientation and similarly, the third passage 2498 may or may not have the same orientation as the fourth passage 24102. 24One or more of the first direction 2408, the second direction 2410, the third direction 2412, and the fourth direction 2414 may have a component that is in the opposite direction from another of on the directions. For instance, the first direction 2408 may, as depicted, be in the opposite direction from the third direction 2412. In some implementations, the first passage 2490 and the second passage 2494 may extend along parallel paths within the housing 2486. Likewise, the third passage 2498 and the fourth passage 24102 may extend along parallel paths within the housing 2486. In other implementations, some or all of the passages may follow non-parallel paths, e.g., the paths may form an X or a + configuration.

The first passage 2490 may be within the housing 2486 and may allow air that is external to the wearable biometric monitoring device to travel from the first vent to the pressure sensor. The first vent 2492, as shown in FIG. 24, may be located on an exterior surface of the housing 2486. The first passage 2490 may be linear, curved, and/or may have a circular cross-section. In some implementations, the first passage 2490 may have a first cross-sectional area at a point along and orthogonal to the first passage 2490. The first cross-sectional area of the first passage 2490 may have a first dimension 24116 in a first measurement direction 24118 and a second dimension 24120 in a second measurement direction 24122, with the first measurement direction 24118 orthogonal to the second measurement direction 24122, as can be seen in FIG. 125, which depicts another view of the general example configuration of the alternative example wearable biometric monitoring device of FIG. 24.

The second passage 2494, third passage 2498, and fourth passage 24102 may by similarly and/or identically configured as described for the first passage 2490. For instance, a cross-sectional area of the second passage 2494 at a point along the second passage 2494 may have a third dimension in a third measurement direction and a corresponding fourth dimension in a fourth measurement direction orthogonal to the third measurement direction; the third passage 2498 may have a fifth dimension in a fifth measurement direction and a corresponding sixth dimension in a sixth measurement direction orthogonal to the fifth measurement direction; and the fourth passage may have a fourth dimension in a seventh measurement direction and a corresponding eighth dimension in an eighth measurement direction orthogonal to the seventh measurement direction. In some implementations, two or more of the four passages of housing 2486 may have the same dimensions, while is some other implementations, none of the four passages may have the same dimensions.

One or more of the four passages may also have different cross-sectional shapes, sizes, and/or configurations from one or more of the four passages. Furthermore, the above discussion and figures regarding the first passage 206 may apply in their entirety to one or more of the four passages of housing 2486.

In this example implementation, the first passage 2490, second passage 2494, third passage 2498, and/or fourth passage 24102 all have substantially circular cross-sections. These cross-sections may, however, also be shapes such as n-gons, squares (with or without rounded corners), ellipses, etc. In some such implementations, the cross-sectional area of each passage may be less than 1 square millimeter. In some other implementations, the first passage 2490, second passage 2494, third passage 2498, and/or fourth passage 24102 may have semicircular cross-sections and/or may have cross-sections that vary in shape/size/aspect ratio along their lengths.

In this example implementation, each of the vents may extend through a different exterior surface of the housing 2486. In some other example implementations, as depicted in FIGS. 24 and 125, more than one vent may extend through the same exterior surface of the housing 2486.

The discussions above, including all the Figures, regarding any of the passages, vents, cover pieces, housing bodies, and their corresponding characteristics and configurations may be combined with or applied to any of the other discussion(s) and/or Figures discussed herein for a similar feature. For instance, while the cross-sections of the passages in FIG. 24 may have a 1:1 aspect ratio, it is also possible to implement these passages so as to have a 2:1 or greater cross-sectional aspect ratio.

In some of the implementations of the present invention, the number of passages and/or vents within a housing is not limited to those examples discussed herein. For instance, the first example wearable biometric device shown in FIGS. 2 through 7 may have more than two passages. In some implementations, each passage may also have more than one vent. For another example, the first passage 206 may have four vents in some implementations.

The housing of the present invention, including, but not limited to, the housing body and cover piece, may be made of various materials. In some implementations, one or more aspects of the housing may be made of a hydrophilic material. In some implementations, one or more aspects of the housing, or the housing itself, may be made of polycarbonate or ABS plastic, which are generally hydrophilic materials. The housing may also be configured such that the surfaces of a passage are hydrophilic. This may be accomplished by applying a hydrophilic coating to the passage and/or manufacturing the passage out of a hydrophilic material. For example, the passage cross-section aspect ratios discussed earlier, e.g., the 2:1 or greater aspect ratios, may encourage any moisture droplets that manage to enter the passage to migrate to one side of the passage or the other due to capillary forces; using a hydrophilic coating may increase the capillary effect and further encourage migration of such moisture droplets to the sides of the passage, leaving the center of the passages clear of moisture.

Among other examples and those discussed above, the present inventors have discovered that passages with specific dimensions and/or in specific configurations may provide the aforementioned benefits. Some such non-limiting examples include: four substantially round passages fluidically connected to the pressure sensor, each with one vent and with a diameter of approximately 1 millimeter; a substantially rectangular passage with a cross-section of approximately 3 millimeters by 1 millimeter, with one vent or with two vents; a substantially rectangular passage with a cross-section of approximately 3 millimeters by 0.3 millimeters and having two vents; a substantially rectangular passage with a cross-section of approximately 2 millimeters by 1 millimeter with one or two vents; a substantially rectangular passage with a cross-section of approximately 2 millimeters by 0.3 millimeters with two vents; and/or a substantially rectangular passage with a cross-section of approximately 2 millimeters by 0.5 millimeters with two vents.

Importantly, the present invention is neither limited to any single aspect nor implementation, nor to any combinations and/or permutations of such aspects and/or implementations. Moreover, each of the aspects of the present invention, and/or implementations thereof, may be employed alone or in combination with one or more of the other aspects and/or implementations thereof. For the sake of brevity, many of those permutations and combinations will not be discussed and/or illustrated separately herein.

What is claimed is:

1. A wearable biometric monitoring device, comprising:
   a pressure sensor;
   a housing that includes a first vent; and
   a first passage in the housing, wherein:
   the first passage provides a first path from the first vent to the pressure sensor,
   the first passage has a first cross-section in a plane perpendicular to the first path at at least a first point along the first path,
   the first cross-section has a first dimension in a first direction and a second dimension in a second direction orthogonal to the first direction, and
   the first dimension is at least one and a half times as large as the second dimension.

2. The wearable biometric monitoring device of claim 1, wherein the first dimension is 2 mm or more.

3. The wearable biometric monitoring device of claim 1, wherein the first direction is tangent to the average exterior surface of the housing at a location closest to the first point.

4. The wearable biometric monitoring device of claim 1, wherein the first dimension is between 2 mm and 4 mm and the second dimension is between 0.3 mm and 1 mm.

5. The wearable biometric monitoring device of claim 1, wherein the first path has a path length of at least 2 mm.

6. The wearable biometric monitoring device of claim 1, wherein the first dimension is greater than 1 mm.

7. The wearable biometric monitoring device of claim 1, wherein the first passage allows air external to the wearable biometric monitoring device to travel from the first vent to the pressure sensor.

8. The wearable biometric monitoring device of claim 1, wherein:
   a portion of an exterior surface of the housing forms a recess, and
   the first vent is located in the recess.

9. The wearable biometric monitoring device of claim 8, wherein:
   the recess is located in the exterior surface of the housing such that the exterior surface of the housing immediately surrounding the recess is adjacent to, and faces towards, a person's skin when the wearable biometric monitoring device is worn,
   the housing further includes:
   a second passage, and
   a second vent that is located on the exterior surface of the housing in a location that is not adjacent to, and does not face towards, the person's skin when the wearable biometric monitoring device is worn;

the second passage provides a second path from the recess to the second vent, the second passage allows air pressure external to the wearable biometric monitoring device to travel from the second vent to the recess, the second passage has a second cross-section in a plane perpendicular to the second path at at least a second point along the second path, the second cross-section has a third dimension in a third direction and a fourth dimension in a fourth direction orthogonal to the third direction, and the third dimension is at least one and a half times as large as the fourth dimension.

10. The wearable biometric monitoring device of claim 9, wherein the recess is configured to allow pressure to travel between the first passage to the second passage even when the wearable biometric monitoring device is worn by the person and the exterior surface of the housing immediately surrounding the recess is thereby covered by the person's skin.

11. The wearable biometric monitoring device of claim 9, wherein:

the recess includes a protrusion within the recess, a gap exists between the protrusion and the sidewalls of the recess, the gap has a gap depth defined by either a height of the protrusion or a depth of the recess and a gap width defined by an offset distance between the sidewalls and the protrusion, and the gap depth is at least one and a half times as large as the gap width.

12. The wearable biometric monitoring device of claim 9, wherein the second path is straight.

13. The wearable biometric monitoring device of claim 9, wherein the second path follows a 2-dimensional curve in a plane normal to the first direction.

14. The wearable biometric monitoring device of claim 9, wherein:

the housing includes a housing body and a cover piece, the second vent is located on the cover piece, and the first passage and the second passage are, at least in part, defined by surfaces of the housing body and the cover piece when the cover piece is assembled to the housing body.

15. The wearable biometric monitoring device of claim 14, wherein the first path follows an interior surface of the cover piece.

16. The wearable biometric monitoring device of claim 1, wherein the first dimension is at least one and a half times the second dimension for the first cross-section at first points located along at least 90% of the first path.

17. The wearable biometric monitoring device of claim 1, wherein the first cross-section varies in shape, size, or dimension along at least a portion of the first path.

18. The wearable biometric monitoring device of claim 1, wherein the first path is straight.

19. The wearable biometric monitoring device of claim 1, wherein the first path follows a 2-dimensional curve in a plane normal to the first direction.

20. The wearable biometric monitoring device of claim 1, wherein the first cross-section is substantially rectangular.

21. The wearable biometric monitoring device of claim 1, wherein the first cross-section is rectangular with internal fillets.

22. The wearable biometric monitoring device of claim 1, wherein:

the housing includes a second vent, the first vent is located at a first location on an outer surface of the housing, the second vent is located at a second location on the outer surface of the housing, the first passage provides a first path from the second vent to the pressure sensor, the first passage allows air external to the wearable biometric monitoring device to travel from the first vent to the pressure sensor, and the first passage allows air external to the wearable biometric monitoring device to travel from the second vent to the pressure sensor.

23. The wearable biometric monitoring device of claim 22, wherein the first dimension is at least three times as large as the second dimension.

24. The wearable biometric monitoring device of claim 22, wherein:

the housing includes a housing body and a cover piece, the first passage is, at least in part, defined by surfaces of the housing body and the cover piece when the cover piece is assembled to the housing body, the first vent extends through the cover piece, the second vent extends through the cover piece or the housing body, and the first location is located such that the first vent is not facing into a person's skin when the wearable biometric monitoring device is worn.

25. A wearable biometric monitoring device, comprising:

a pressure sensor; and a housing, the housing including:

a pressure sensor plenum volume in fluidic communication with the pressure sensor, a first passage, with a first vent on an exterior surface of the housing, that allows air pressure external to the wearable biometric monitoring device to travel from the first vent to the pressure sensor, a second passage, with a second vent on the exterior surface of the housing, that allows air pressure external to the wearable biometric monitoring device to travel from the second vent to the pressure sensor, a third passage, with a third vent on the exterior surface of the housing, that allows air pressure external to the wearable biometric monitoring device to travel from the third vent to the pressure sensor, and a fourth passage, with a fourth vent on the exterior surface of the housing, that allows air pressure external to the wearable biometric monitoring device to travel from the fourth vent to the pressure sensor, wherein:

the first passage extends away from the pressure sensor plenum volume in a first direction, the second passage extends away from the pressure sensor plenum volume in a second direction, the third passage extends away from the pressure sensor plenum volume in a third direction, the fourth passage extends away from the pressure sensor plenum volume in a fourth direction, the first passage has a first dimension in a third direction and a corresponding second dimension in a fourth direction orthogonal to the third direction, the second passage has a third dimension in a fifth direction and a corresponding fourth dimension in a sixth direction orthogonal to the fifth direction, the third passage has a fifth dimension in a seventh direction and a corresponding sixth dimension in a eighth direction orthogonal to the seventh direction, the fourth passage has a seventh dimension in a ninth direction and a corresponding eighth dimension in a tenth direction orthogonal to the ninth direction, two or more of the first dimension, the third dimension, the fifth dimension, and the seventh dimension are within ±10% of each other, and two or more of the second dimension, the fourth dimension, the sixth dimension, and the eighth dimension are within ±10% of each other.

26. The wearable biometric monitoring device of claim 25, wherein the first passage, the second passage, the third passage, and the fourth passage all have substantially circular cross-sections with cross-sectional areas of less than 1 square millimeter.

27. The wearable biometric monitoring device of claim 25, wherein:
the first direction and the second direction are parallel paths within the housing, and
the third direction and the fourth direction are parallel paths within the housing.

28. The wearable biometric monitoring device of claim 25, wherein one or more of the first passage, the second passage, the third passage, and the fourth passage have a semicircular cross-section.

29. The wearable biometric monitoring device of claim 25, wherein more than one of the first direction, the second direction, the third direction, and the fourth direction are parallel with one another.

30. The wearable biometric monitoring device of claim 25, wherein:
three or more of the first dimension, the third dimension, the fifth dimension, and the seventh dimension are within ±10% of each other; and
three or more of the second dimension, the fourth dimension, the sixth dimension, and the eighth dimension are within ±10% of each other.

* * * * *